United States Patent
Xu et al.

(10) Patent No.: US 7,611,840 B2
(45) Date of Patent: Nov. 3, 2009

(54) METHOD AND DEVICE FOR THE TREATMENT OF BIOLOGICAL SAMPLES

(75) Inventors: Guolin Xu, Singapore (SG); Pei-Lin Mao, Singapore (SG); Yuan Hong Yu, Singapore (SG); Eng Hock Francis Tay, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1037 days.

(21) Appl. No.: 10/910,961

(22) Filed: Aug. 3, 2004

(65) Prior Publication Data
US 2006/0030796 A1   Feb. 9, 2006

(51) Int. Cl.
C12Q 1/68 (2006.01)
C12P 19/34 (2006.01)
C12N 13/00 (2006.01)
C12M 1/42 (2006.01)
C12M 1/34 (2006.01)
B01F 11/02 (2006.01)
H01L 41/083 (2006.01)

(52) U.S. Cl. .................... 435/6; 435/91.2; 435/173.7; 435/259; 435/287.2; 435/288.5; 435/306.1; 366/127; 241/2; 310/338

(58) Field of Classification Search .............. 435/306.1, 435/288.5, 6, 91.2, 173.7, 259, 287.2; 366/127; 241/2; 310/338
See application file for complete search history.

(56) References Cited

U.S. PATENT DOCUMENTS

| | | | |
|---|---|---|---|
| 4,721,106 A | 1/1988 | Kurtze et al. | 128/328 |
| 5,922,591 A * | 7/1999 | Anderson et al. | 435/287.2 |
| 6,100,084 A | 8/2000 | Miles et al. | 435/306.1 |
| 6,391,541 B1 | 5/2002 | Petersen et al. | 435/5 |

(Continued)

FOREIGN PATENT DOCUMENTS

DE   3425992   1/1986

(Continued)

OTHER PUBLICATIONS

Belgrader, P., et al., "A Microfluidic Cartridge to Prepare Spores for PCR Analysis," *Biosens Bioelectron.* 14(10-11):849-52, Jan. 2000.

(Continued)

*Primary Examiner*—William H Beisner
(74) *Attorney, Agent, or Firm*—Seed IP Law Group PLLC

(57) ABSTRACT

A device for sample tissue disruption and/or cell lysis comprising: a piezoelectric material; and at least a second material in contact with the piezoelectric material; and wherein the second material has an uneven surface on an opposite side to that in contact with the piezoelectric material. The device may be made by assembling at least three layers and membranes for the valves and pumps. The piezoelectric material is actuated by an external voltage source to generate cavitation, which disrupts tissue and/or lyses cells, in particular by a modulated alternative external voltage. The invention further provides a method of disrupting tissue and/or lysing cells in a device. Also provided is a piezoelectric device comprising a piezoelectric material in contact with a second material, and wherein the second material has an uneven surface on an opposite side to that in contact with the piezoelectric material.

33 Claims, 17 Drawing Sheets cross section view for the cartridge

U.S. PATENT DOCUMENTS

| | | | |
|---|---|---|---|
| 6,411,208 B1 | 6/2002 | Buess et al. | |
| 6,699,711 B1 | 3/2004 | Hahn et al. | 435/283.1 |
| 6,948,843 B2 * | 9/2005 | Laugharn et al. | 366/127 |
| 2004/0209354 A1 * | 10/2004 | Mathies et al. | 435/287.2 |

FOREIGN PATENT DOCUMENTS

| | | |
|---|---|---|
| DE | 19820466 | 11/1999 |
| FR | 2845618 | 4/2004 |
| JP | 1124966 A | 5/1989 |
| JP | 2002206852 A | 7/2002 |
| JP | 2002318193 | 10/2002 |
| TW | 469046 | 12/2001 |
| TW | 550066 B | 9/2003 |
| WO | 0108237 A1 | 2/2001 |
| WO | WO 01/08237 | 2/2001 |
| WO | WO 01/46714 | 6/2001 |
| WO | WO 2004/046305 A2 | 6/2004 |

OTHER PUBLICATIONS

Belgrader, P., et al., "A Minisonicator to Rapidly Disrupt Bacterial Spores for DNA Analysis," *Anal Chem.* 71(19):4232-6, Oct. 1, 1999.

Gascoyne, P., et al., "Microsample Preparation by Dielectrophoresis: Isolation of Malaria," *Lab Chip* 2(2):70-5, May 2002.

Liu, R., et al., "Self-contained, Fully Integrated Biochip for Sample Preparation, Polymerase Chain Reaction Amplification, and DNA Microarray Detection," *Anal Chem.* 76(7):1824-31, Apr. 1, 2004.

Liu, R., et al., "Hybridization Enhancement Using Cavitation Microstreaming," *Anal Chem.* 75(8):1911-7, Apr. 15, 2003.

Taylor, M., "Lysing Bacterial Spores by Sonication Through a Flexible Interface in a Microfluidic System," *Anal Chem.* 73(3):492-6, Feb. 1, 2001.

Anonymous, "Ultrasonic probe for rapid processing of small liq. samples minimising tip erosion and heating—has specified concavity at tip to focus sound field and overcome edge sound dispersion effects", Derwent Abstract Accession No. 93-342956/43, Research Disclosure 353012A, Sep. 10, 1993.

\* cited by examiner cross section view for the cartridge (A)

(B)

(A)

(B)

(A)

(B)

detail of the dissociation chamber integrated in the chip (without sample inside)

detail of the dissociation chamber integrated in the chip

METHOD AND DEVICE FOR THE TREATMENT OF BIOLOGICAL SAMPLES

FIELD OF THE INVENTION

The present invention relates to devices for the treatment of biological samples. In particular, the invention relates to cartridges and/or biochip devices comprising a piezoelectrical material for the treatment of biological tissues and/or cells.

BACKGROUND OF THE INVENTION

A tissue usually contains cells inside a biological matrix, which provides mechanical strength to the tissue. The tissue disruption and cell lysis steps are required for isolating cells, nucleic acids or proteins from the tissue.

Conventional tissue disruption and cell lysis processes are time-consuming and labour-intensive. They employ motorised mechanical homogenisers that have a blender-like component to generate shear force, which physically breaks up the solid tissues and release the cells within. Following this, the cells are subjected to chemical, mechanical or thermal treatment to lyse the cells in order to extract the intercellular and/or intracellular components.

Other ways of tissue disruption adaptable for use with micromechanical and/or automated processes are available which employ enzymolytic tissue disruption methods (WO 2004/046305 incorporated by reference herein).

Disruption of spores and cells by sonification has also been reported [P. Belgrader et. al., *Anal. Chem.*, 1999, 71:4232-4236; Belgrader et. al., *Biosensors and Bioelectronics*, 2000, 14:849-852; Taylor et. al., *Anal. Chem.*, 2001, 73:492-496]. However, these are applicable for cell lysis and are not feasible for disrupting tissue. Further, the sonicating devices are external devices and are not integrated in an automated system such as μ-TAS or MEMS.

Piezoelectric material has been used as an external means for actuation to bring about cell lysis [P. Belgrader et. al., *Anal. Chem.*, 1999, 71:4232-4236]. However, a high voltage is usually required to actuate the piezoelectric material and further, due to the material's heat conduction, an insulant is required to prevent an increase in temperature from degrading the cells. This makes it difficult to incorporate the piezoelectric material in a micro device.

A fully-integrated biochip for the detection of pathogenic bacteria has also been reported [R Liu et. al., *Anal. Chem.*, 2004, 76(7):1824-1831]. The piezoelectric disc in the biochip only serves to increase the mixing efficiency of fluids within the biochip. It also comprises electrical connections and a printed circuit board within the chip. The presence of electrochemical pumps, and electrical connections integrated within the biochip make the biochip too expensive for mono-use (disposable) applications.

There is therefore a need in this field for inexpensive disposable devices useful for the treatment of biological sample, in particular biological tissues.

SUMMARY OF THE INVENTION

The present invention addresses the problems above and provides an easy to use, inexpensive and efficient device for the treatment of biological samples.

According to a first aspect, the invention provides a device for sample tissue disruption and/or cell lysis comprising a piezoelectric material.

In particular, the piezoelectric material is driven by frequency modulated alternative voltage.

The piezoelectric device of the invention comprises: a piezoelectric material; and at least a second material in contact with the piezoelectric material; and wherein the second material has an uneven surface on an opposite side to that in contact with the piezoelectric material. The uneven surface improves the cavitation effect.

The second material is preferably attached to the piezoelectric material. In particular, the second material is glued or fastened to the piezoelectric material. The uneven surface may be made according to any standard method, for example, it may be brought about by a layer of silica beads. For example, the layer of silica beads is attached to the surface of the second material on an opposite side to that in contact with the piezoelectric material. The silica beads may have a diameter between 100 and 400 μm.

The second material may be any suitable material, in particular the second material has a Young's modulus of between 50 to 220 Gpa. The second material may be made of metal or polymer material. For example, the metal can be chosen from a group comprising steel, stainless steel, brass, copper and aluminium. The polymer material can be chosen from a group comprising polycarbonate, poly(methyl methacrylate) (PMMA), polyethylene, polypropylene, polystyrene and poly vinyl chloride (PVC).

The piezoelectric material may be in the form of a disc, rod or bar or has a planar shape with at least 3 sides.

The device may comprise means to actuate the piezoelectric material, for example two electrodes applied, attached or connected to the piezoelectric material.

The device is, in particular disposable.

According to another aspect, the device of the invention is a cartridge. The cartridge may further comprise an inlet port, and outlet port, and at least one chamber. The cartridge may be used as it is or may be incorporated or integrated into a biochip, such as in a micro total analytical system (μ-TAS) or a lab-on-a-chip system. In particular, the cartridge of the invention is a disposable cartridge.

According to another aspect, the device is a biochip device and further comprises:
- a dissociation chamber;
- reagent and buffer reservoir(s);
- one or more valves;
- one or more pumps; and- channels connecting the chamber, reservoir(s) and valve(s).

The biochip device can be used for bio-sample preparation.

The device may further comprise a micropump, a binding and mixing chamber and/or an extraction/elute/PCR chamber. The binding and mixing chamber may also comprise a piezoelectric material and a second material in contact with the piezoelectric material. The second material may comprise an uneven surface on an opposite side to that in contact with the piezoelectric material. The uneven surface may be brought about by a layer of silica beads. The device may further comprise valves, which may be microvalves. The microvalves may be poly(dimethylsiloxane) (PDMS) membrane microvalves. The micropump may comprise a membrane. The membrane may be a poly(dimethylsiloxane) (PDMS) membrane.

According to another aspect, the device may further comprise an injection hole. The device may also be modified such that automatic pumping can be carried out.

According to one aspect, the biochip device employs external pneumatic actuator(s) to actuate pumps and valves, which are integrated inside the chip.

The extraction/elute/PCR chamber may be deposited with magnetic material, for example with permalloy, more in particular, with permalloy pins.

The binding and mixing chamber may comprise beads coated with at least one linker for binding to nucleic acid molecules. The beads may be magnetic beads.

The device may be made of polymeric material, for example polycarbonate.

The device may also comprise biosensors, RT-PCRs and microarrays integrated into the chip.

According to another aspect, the biochip device is composed of at least three layers, one or more membranes for the valves and one or more membranes for the pumps. The first layer comprises at least the dissociation chamber, reagent and buffer reservoir(s), the second layer comprises at least the piezoelectric material, and wherein the valves and the pumps are found at an interface between the second and third layers, and the channels are found at the interfaces of the first and second, and the second and third layers.

The biochip may further comprise a cover to put over the first layer.

According to another aspect, the invention provides a method of disrupting tissue and/or lysing cells in a device comprising the steps:
  loading a sample and reagents;
  actuating a piezoelectric material, wherein the piezoelectric material is in contact with a second material, and wherein the second material has an uneven surface on an opposite side to that in contact with the piezoelectric material, the uneven surface contacting the sample;
  obtaining disrupted tissue and/or lysed cells; and
  recovering the eluate.

The uneven surface may be brought about according to any standard method, for example, it may be brought about by a layer of silica beads. The silica beads may have a diameter between 100 and 400 μm.

According to the method of the invention, the piezoelectric material is actuated by an external voltage source. The external voltage source may supply sinusoidal wave voltage. The sinusoidal wave voltage may be any suitable wave voltage, for example, it may have a peak-to-peak voltage from −140V to +140V. However, the peak-to-peak voltage is not limited to these specific values. The sinusoidal wave voltage has a modulating frequency. The sinusoidal wave voltage may be for example from 1.0 kHz to 20 kHz. In particular, the external voltage source supplies a frequency modulated voltage to actuate the piezoelectric material.

The biological sample may be a tissue from animal, human, plant, bacterial or virus and/or cell sample. The sample may be fresh or frozen tissue and/or cell sample. According to another aspect of the present embodiment, the sample is culture cell, whole blood cell, serum, urine, saliva or tissue from biopsies.

According to the method of the invention, the actuation of the piezoelectric material generates impact and cavitation to bring about the tissue disruption and/or cell lysis.

According to another aspect, the method of the invention further comprises the steps of isolating, purifying and/or amplifying nucleic acids obtained from the disrupted tissue and lysed cells, and recovering the nucleic acids. The nucleic acids may be recovered from the disrupted and/or lysed cells by adding beads coated with at least one linker, and wherein the binding of the linker on the beads to the nucleic acids is carried out by actuating a second piezoelectric material to increase the mixing and binding efficiency, and recovering nucleic acids linked to the beads.

According to another aspect, the invention also provides a piezoelectric device comprising a piezoelectric material, which is in contact with at least a second material; and wherein the second material has an uneven surface on an opposite side to that in contact with the piezoelectric material. The piezoelectric device may be used in the cartridge and/or biochip device of the invention.

The figure shows a longitudinal (cross) sectional view for the reservoir, pump, valve, channel and chamber connection.

Figure 11A:
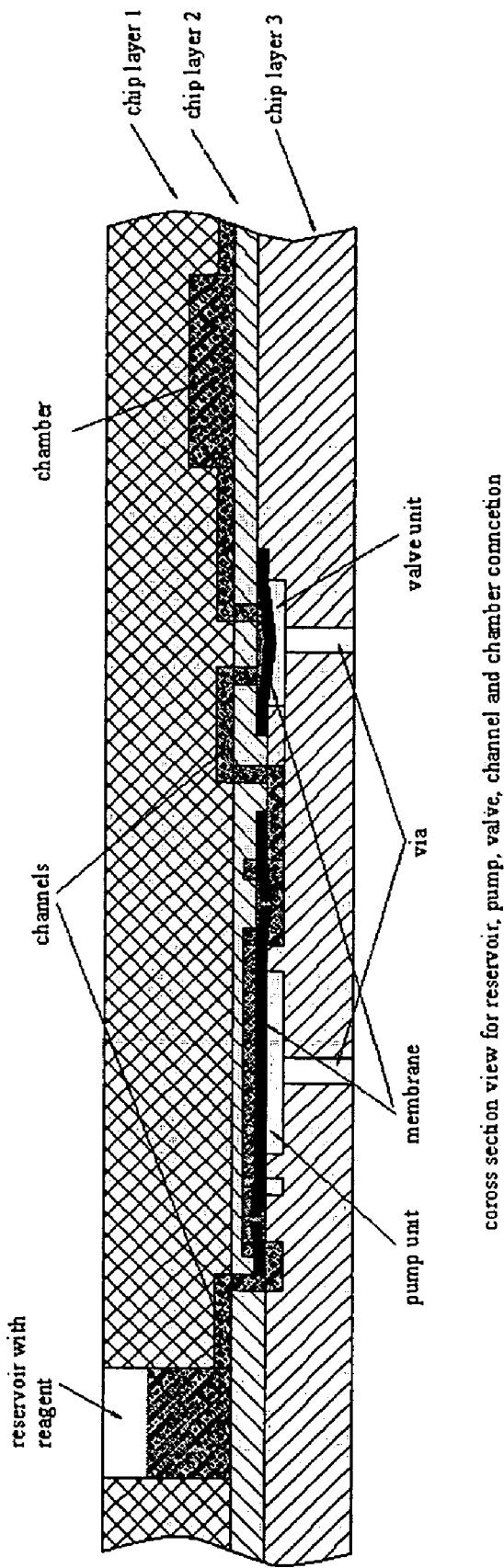
FIG. 11A shows the structure of a biochip device comprising three layers.
Figure 11B:
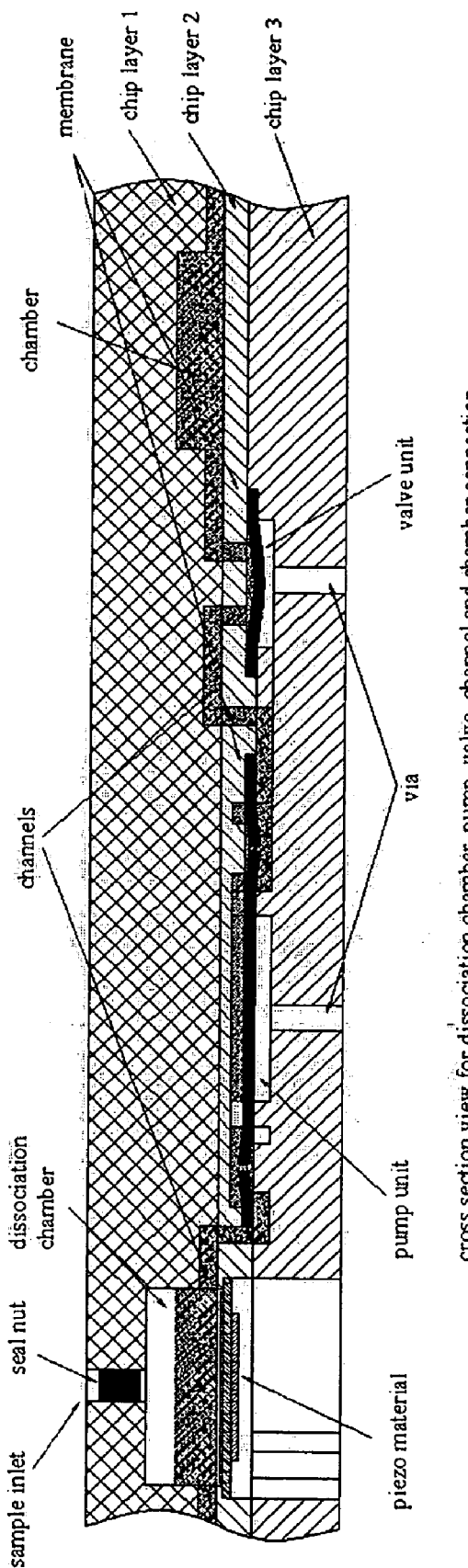

FIG. 11B shows the structure of a biochip device comprising three layers. The figure shows a different longitudinal (cross) sectional view for the dissociation chamber, pump, valve, channel and chamber connection.

Figure 12A:
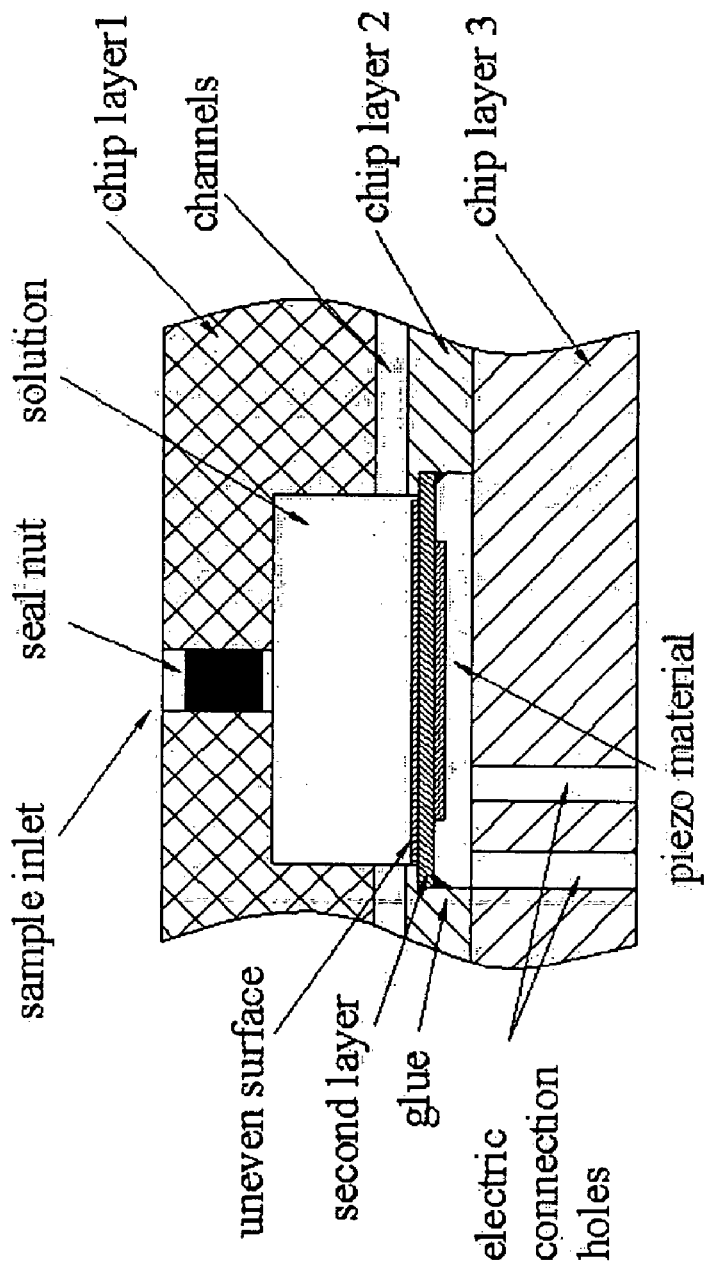

FIG. 12A shows a detailed view of the dissociation chamber of FIG. 11B, wherein the dissociation chamber has no sample inside.

Figure 12B:
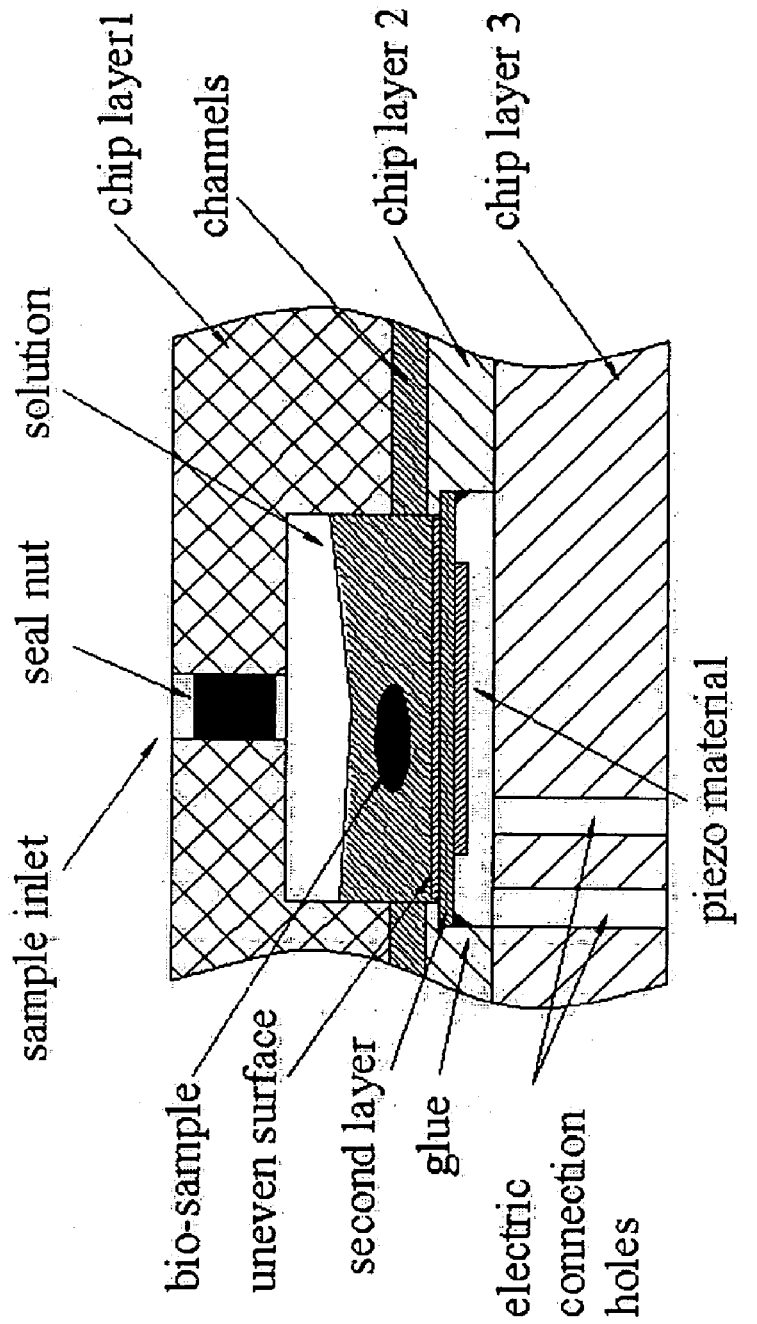

FIG. 12B shows a detailed view of the dissociation chamber of FIG. 11B, wherein the dissociation chamber has a bio-sample and solution inside.

Figure 13:
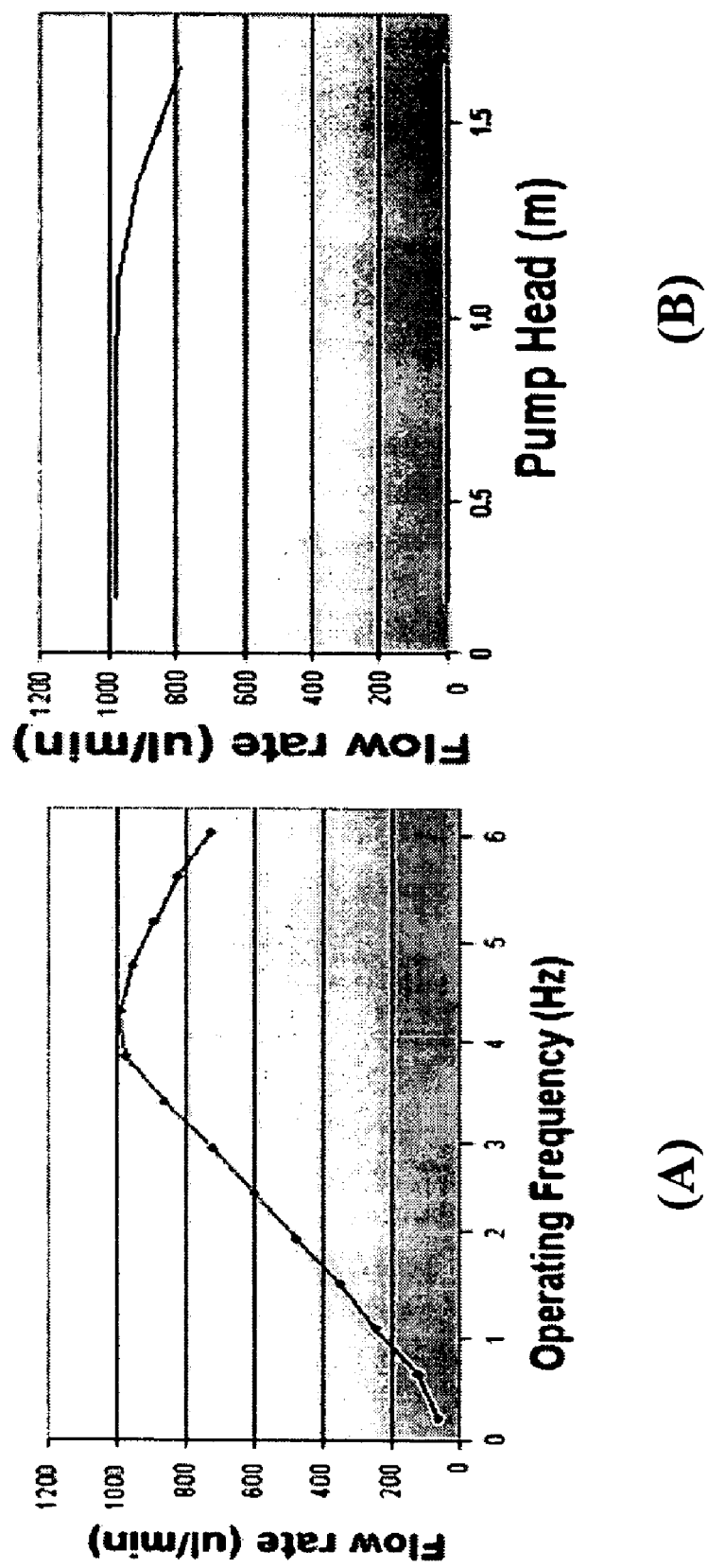

FIGS. 13 (A), (B) show experimental results of the flow rate vs. driving frequency and the flow rate vs. pressure characteristic. (B) operating frequency (Hz); (B) pump head.

Figure 14:
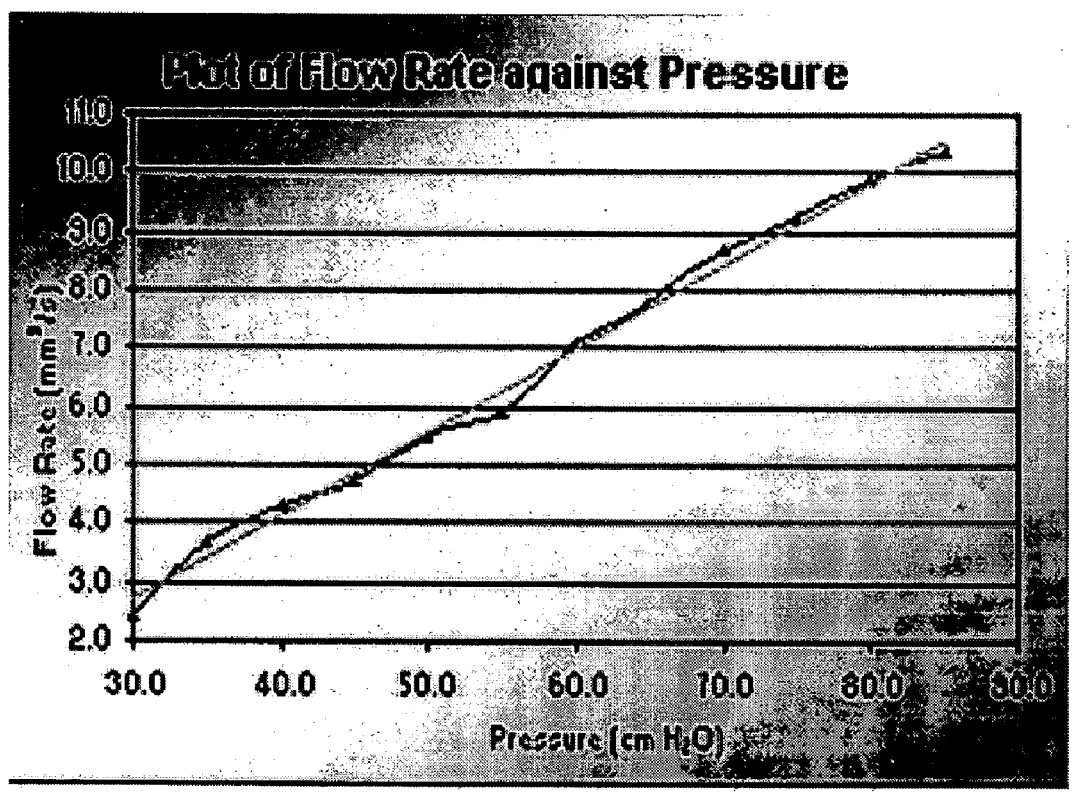

FIG. 14 shows the flow rate against pressure of the microvalve when it is open.

DETAILED DESCRIPTION OF THE INVENTION

The present invention provides devices, for example, a cartridge and/or biochip device, for the efficient treatment of biological samples, like culture cell, whole blood cell, serum, urine, saliva, tissue and tissue from biopsies, which can be used as the raw sample for preparing the bio-molecular sample, such as purified DNA and RNA, for gene-related assays.

The devices of the invention are particularly useful for the treatment of tissue samples with a wide range of size, which need to be disrupted before the extraction of the genes of interest. In particular, the devices of the invention use a piezoelectric device for the disruption of the tissue sample by adapting a technique based on the principle of cavitation [Liu R. H., et al., *Anal. Chem.*, 2003, 75: 1911-1917; and Liu R. H., et al., Lab Chip, 2002, 2(3), 151-157]. The devices of the invention allow simultaneous tissue disruption and cell lysis. However, the devices of the invention can also be used just for the treatment (lysis) of culture cell, whole blood cell, serum, urine, saliva.

According to one embodiment, the devices of the invention are disposable. Accordingly, the devices of the invention are inexpensive and particularly suitable for mono-use (disposable) applications.

According to a first aspect, the invention provides a device for sample tissue disruption and/or cell lysis comprising a piezoelectric device.

The piezoelectric device of the invention comprises: a piezoelectric material; and at least a second material in contact with the piezoelectric material; and wherein the second material has an uneven surface on an opposite side to that which is in contact with the piezoelectric material. The uneven surface improves the cavitation effect.

According to another aspect, the device of the invention is a cartridge (also referred to biochip cartridge) comprising the piezoelectric device for sample tissue disruption and/or cell lysis. The cartridge may further comprise an inlet port, an outlet port, and at least one chamber. The cartridge further comprises a chamber where the tissue disruption and/or cell lysis is carried out. The cartridge may be used as it is or may be incorporated or integrated into a biochip, such as in a micro total analytical system (µ-TAS) or a lab-on-a-chip system. In particular, the cartridge of the invention is a disposable cartridge.

According to another aspect, the device is a biochip device.

Accordingly, the device of the invention utilises a piezoelectric material (PZT) as an actuator to generate both strong impact and cavitation for fresh frozen tissue disruption and/or cell lysis.

Embodiments of the cartridge and/or biochip devices of the invention will be better understood by reference to the figures which are provided by way of illustration, and are not intended to be limiting of the present invention. Further, with reference to the method of treating a biological sample by actuating the PZT device using an external source, the method can be applied to both the cartridge and the biochip device of the invention.

Cartridge

Figure 1A:
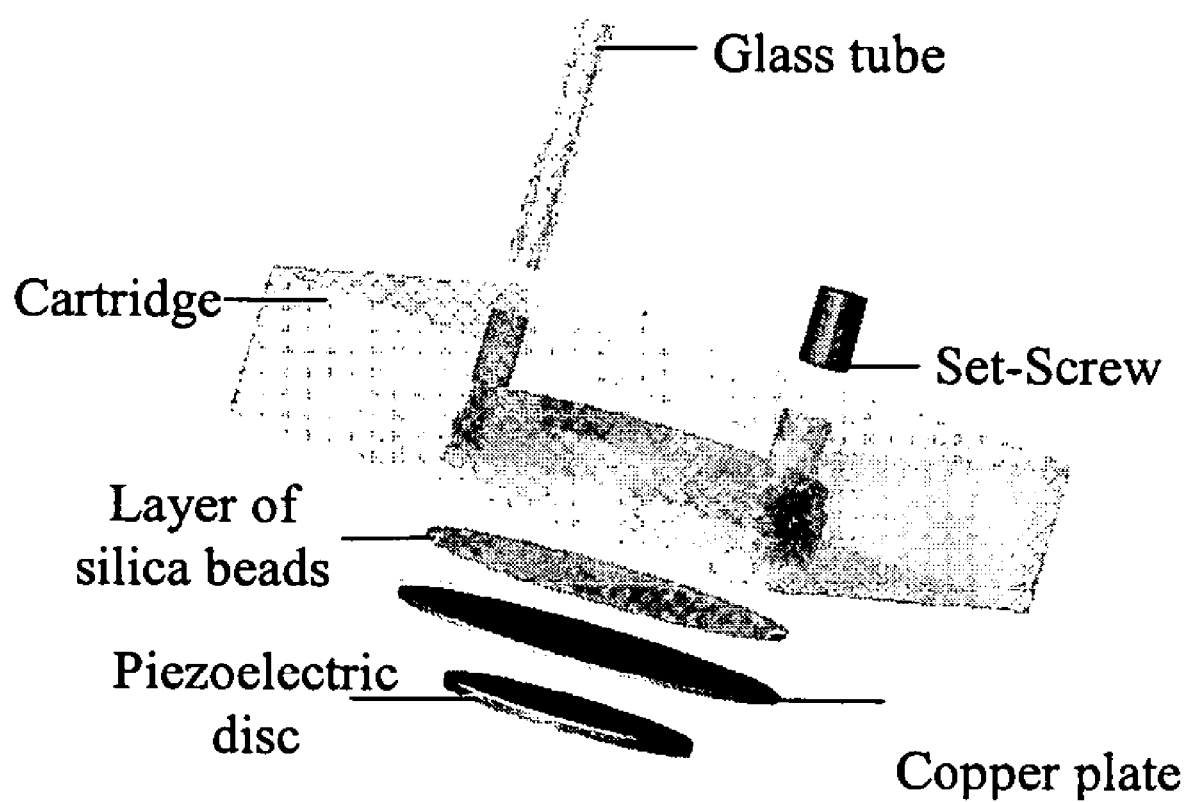
FIG. 1A is an exposed view of the cartridge device.
Figure 1B:
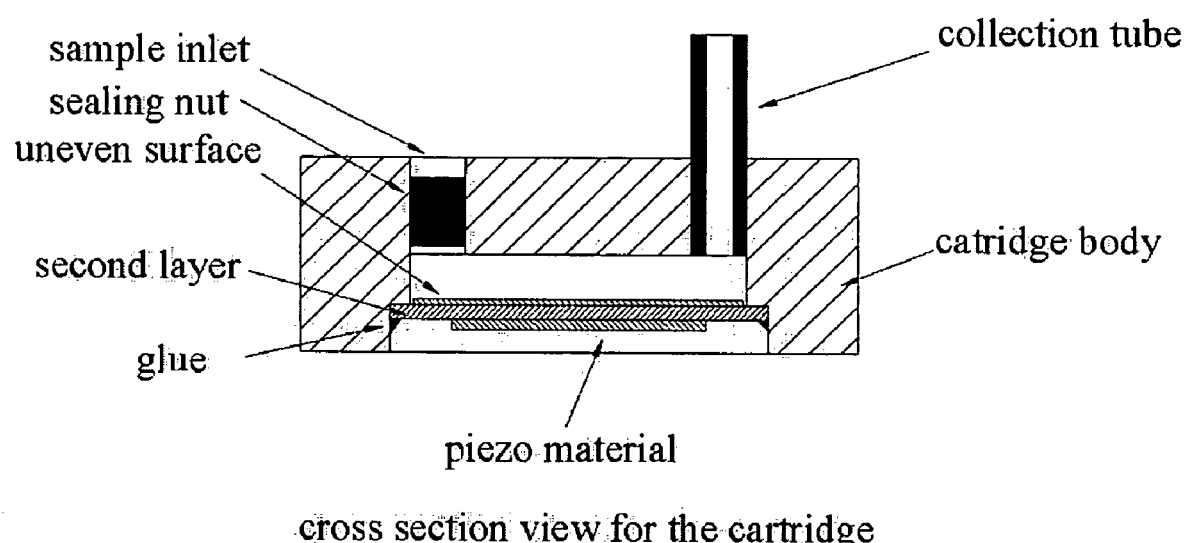
FIG. 1B is a cross sectional view of the cartridge device.
Figure 2:
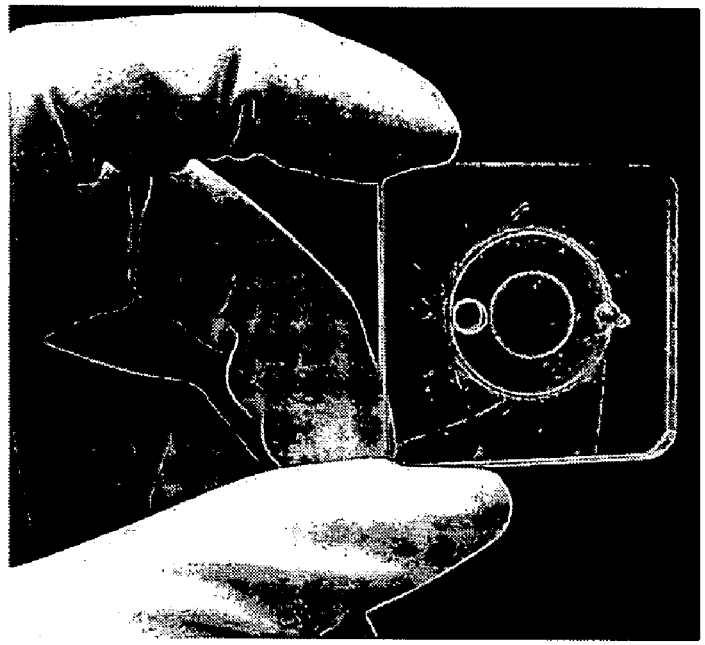
FIG. 2(A) is a photograph of the prototype of the cartridge device.
FIG. 2(B) shows a driver circuit chassis (body) used for the cartridge and biochip devices of the inventions.
Figure 2:

FIG. 1A is an exposed view of the cartridge of the invention. A longitudinal (cross)-sectional view of the cartridge is shown in FIG. 1B. FIG. 2 is a photograph of a prototype of the cartridge of FIG. 1. It has an outer dimension of 25 m by 25 mm by 6 mm. However, the cartridge of the invention is not limited to these dimensions. A skilled person in the art would be able to choose the dimensions according to the specific use of the cartridge.

Figure 9:
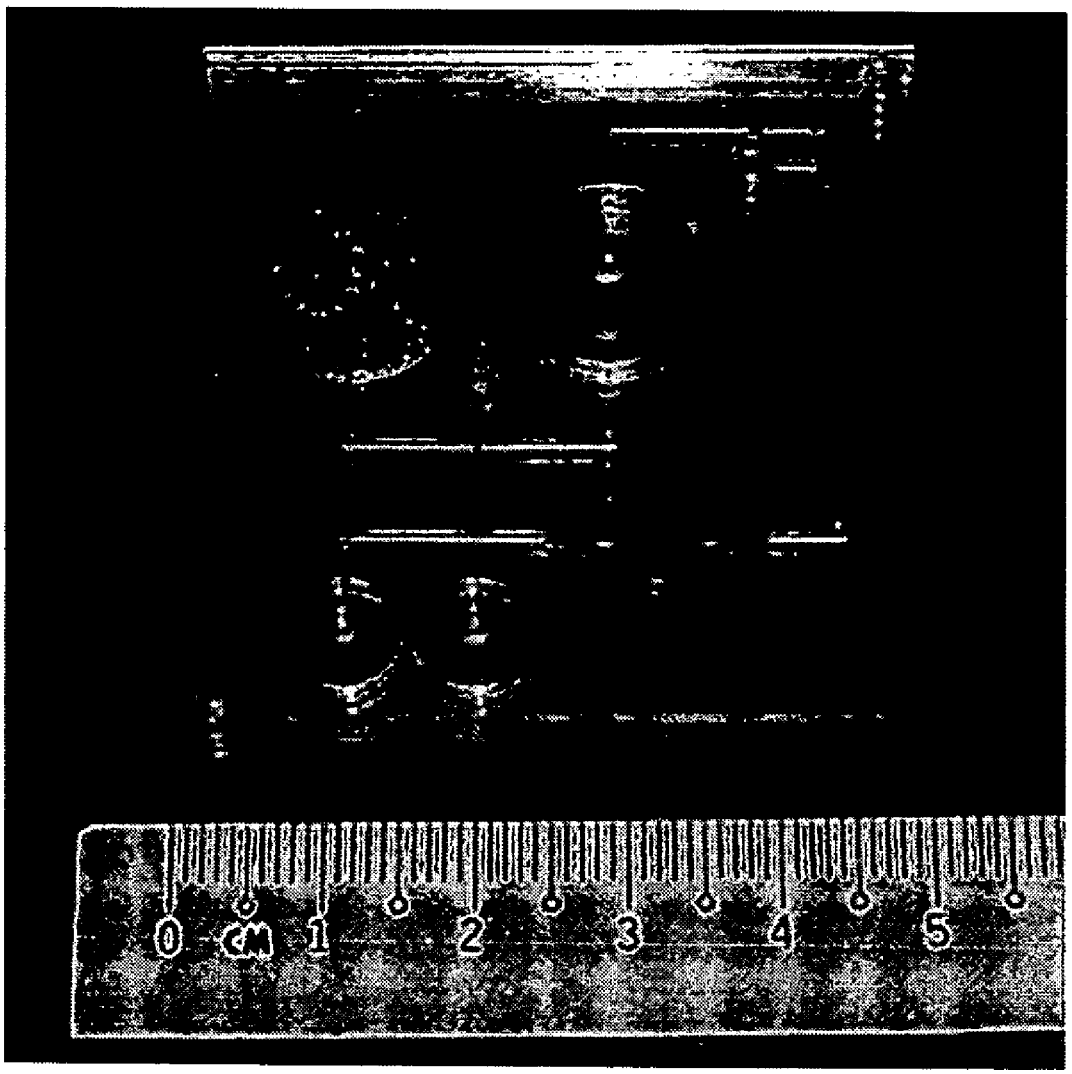
FIG. 9 shows an embodiment of the biochip device.

As shown in FIGS. 1, 2, and 9, the cartridge and/or biochip device of the invention is transparent, so that the disruption process can be easily observed and verified.

The cartridge comprises an inlet port for the input of biological sample and reagents. FIG. 1 shows an inlet fabricated on the sidewall of the chamber of the cartridge. However, it will be understood by a skilled person that any known manner of fabricating an inlet may be used. The cartridge is provided with sealing means for sealing the inlet port after the required biological sample and/or reagents have been introduced. FIG. 1 shows a set-screw (sealing nut) of 4 mm used to seal the inlet port. The size of the set-screw will be chosen according to the size and diameter of the inlet port. The cartridge also comprises an outlet port for the withdrawal of the sample solution after the tissue disruption and/or cell lysis has been carried out. In the particular example shown in FIG. 1A, a 1.5 mm outer diameter glass tube is glued to the chamber to act as the outlet tube for the disrupted sample solution to be withdrawn. This tube will connect to a 1 ml syringe so that the solution obtained after the disruption is completed can be collected. However, it will be apparent to any skilled person that the outlet port can be fabricated and/or applied to the cartridge according to any method known in the art.

The cartridge comprises a piezoelectric material in contact with a second material, wherein the second material has an uneven surface on an opposite side to that in contact with the piezoelectric material. In particular, the piezoelectric material is attached to the second material by using any suitable means known in the art. The PZT is, for example, glued or fastened to the second material.

The second material can be any suitable material, for example, a metal, polymer material, glass, or the like. The second material can be any metal, for example, selected from the group consisting of steel, stainless steel, brass, copper and aluminium. The second material can be any suitable polymer, for example, selected from a group consisting of polycarbonate, poly(methyl methacrylate) (PMMA), polyethylene, polypropylene, polystyrene and poly vinyl chloride (PVC). It is important that the second material maintains a certain rigidity or resistance in order to endure the bending of the piezoelectric material when the piezoelectric material is actuated. In particular, the second material has a Young's modulus [number representing (in pounds per square inch or dynes per square centimeter) the ratio of stress to strain for wire, bar or for a structure of any shape, of a given material] of between 50 to 220 GPa. Therefore, according to a particular aspect, any material having a Young's modulus of between 50 to 220 GPa may be used as the second material for the cartridge. When the second material is a metal, the PZT and second material may be glued together by means of electrical conductive glue. The second material may also be fastened to the PZT material by suitable means known in the art.

The second material comprises an uneven surface, which is in contact with the biological sample. According to a first technical approach, the surface of the second material in contact with the sample is worked so as to create an uneven surface. According to another approach, the uneven surface is brought about by a layer of silica beads. The silica beads may be those used in water jet machining (an industrial process using high pressure water jet from a nozzle to cut materials). They may have very sharp edges. The silica beads may have any size, for example, with a diameter between 100 and 400 µm. However, it will be evident to a skilled person how to make and bring about an uneven surface according to any method known in the art.

In FIG. 1A, a brass or cotton disc with a thickness of 0.2 mm and a diameter of 15 mm is first covered with a thin layer of glue. Silica beads are then placed on the thin layer of glue and cured in an oven for one hour at 70° C. A 10 mm diameter PZT disc (PXE5 from PHILIPS™) is then glued onto the other side of the brass disk to act as an actuator. However, it will be evident to a skilled person that the PZT is not limited to the shape of a disc, but can be a rod, a bar, or any other structure having a planar shape with at least 3 sides, for example, having a planar shape of a triangle, square, rectangular, and so on.

The cartridge can be made of any suitable material, for example, polycarbonate. Polycarbonate may be used to fabricate the cartridge by computer numeric control (CNC) machining. The cartridge also comprises a chamber where the disruption of the tissue and/or lysis of the cells are carried out. The chamber shown in FIGS. 1 and 2 has a dimension of 14.5 mm diameter and 1 mm depth. However, the dimension of the chamber may be adapted according to specific requirements. The total volume of the cartridge shown in FIGS. 1 and 2 is about 165 µl.

The piezoelectric material is actuated by an external voltage source. Accordingly, the PZT material provides a means of actuation, for example, two electrodes connected to the external voltage source. When the second material is a metal, one electrode will be connected to the PZT material and the second electrode connected to the second material. However, when the second material is a non-conductive material, like a polymer material, then the two electrodes will be connected to the PZT material. The means for connections of electrodes applied on the PZT will preferably not be integrated into the cartridge.

Once the PZT material is actuated by the external source, the PZT material and the second material generate bubbles in the biological sample solution. This phenomenon is known as cavitation. The second material has an uneven surface, preferably a layer of silica beads, which improves the generation of bubbles, as well as the lysis of the tissue. The bubbles act on the biological sample, causing the disruption of the tissue and/or the lysis of the cells. Accordingly, when the biological sample is a tissue, for example a tumour, the disruption of the tissue and lysis of the cells are carried out simultaneously. The disruption and lysis may be carried out within 5-40 seconds, depending on the type of biosample.

As mentioned above, Liu R. H., et al., *Anal. Chem.*, 2004, 76:1824-1831, discloses a fully integrated biochip comprising a PZT disc to enhance the mixing and binding of target bacterial cells inoculated in blood with immunomagnetic capture beads, by means of the microstreaming technique. On the contrary, the PZT material of the cartridge and biochip device of the present invention is used for a totally different purpose. In the present invention, the purpose is for the disruption of tissue and lysis of cells.

In order to actuate the PZT material to generate cavitation, the present inventors have built a driver circuit that is capable of generating a sinusoidal voltage that has a continuously changing frequency. The specifications of this driver circuit are defined as follows:

adjustable peak to peak AC voltage, $V_o$;
adjustable fundamental, mean frequency, $f_m$;
adjustable oscillating frequency component, $\Delta f_o$.

The oscillating frequency component is designed to be continuously varying at 3.3 Hz. This means the instantaneous driving frequency is given by:

$$f=f_m+\Delta f_o \sin(w_s t), \text{ where } w_s=2\pi(3.3 \text{ Hz})$$

The fundamental frequency, $f_o$, is usually selected to be the natural frequency of the piezoelectric material. This value can be derived accurately through experiments by exciting the piezoelectric material with a range of sinusoidal input (having different frequencies). At resonance, the piezoelectric material vibrates most vigorously.

Figure 3:
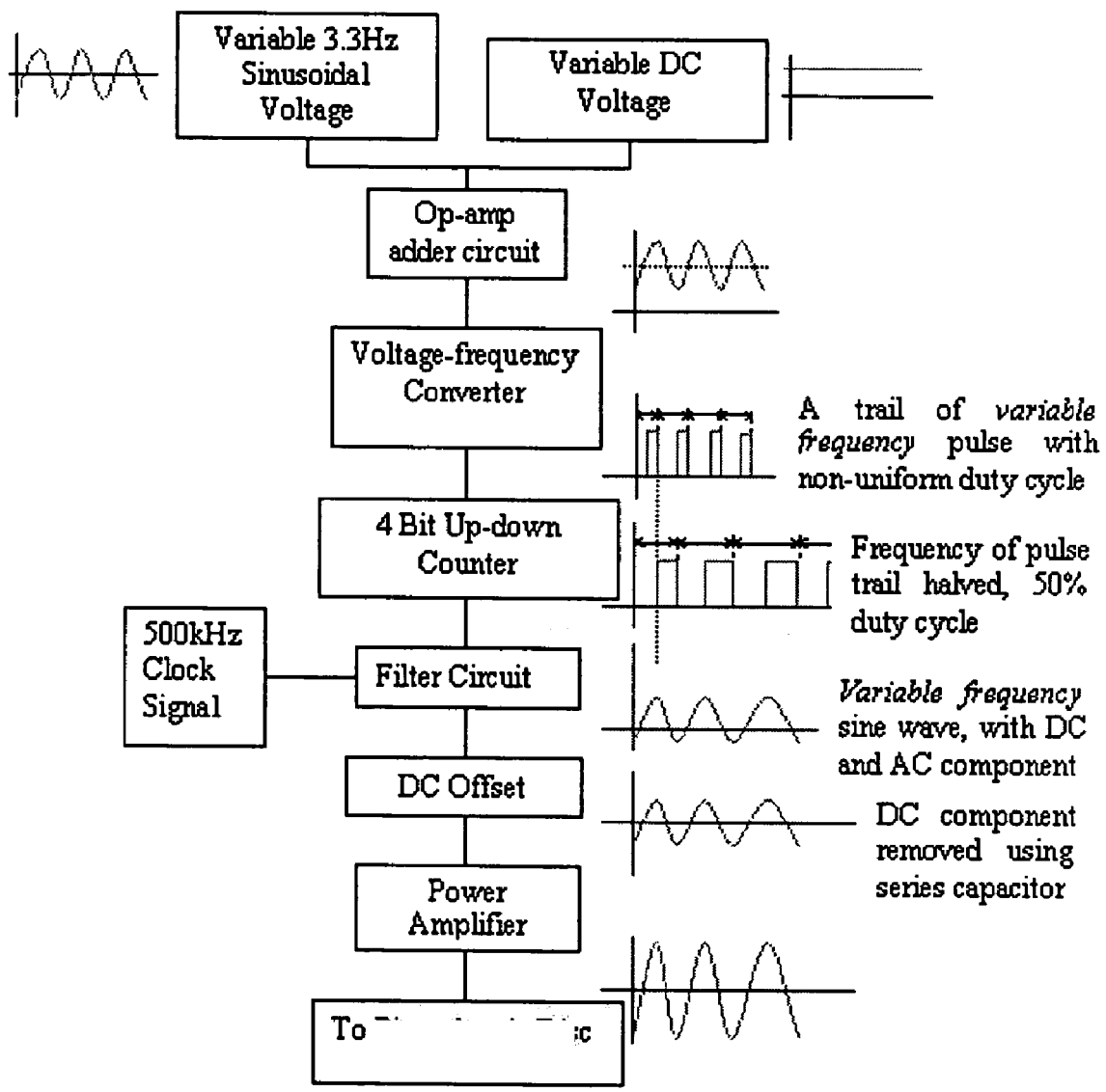
FIG. 3 is a circuit topology showing the working principle of the scanning frequency high voltage power supply.

The circuit topology is depicted in FIG. 3. The output waveform at various stages and its symbol are also shown.

FIGS. 2(A) and 2(B) display a prototype of a miniature cartridge and driver circuit chassis, respectively. In a preferred embodiment, when driving the cavitation cartridge, the oscillating frequency component is first set to zero. The natural frequency is adjusted to 6.1 kHz and verified via an oscilloscope in FFT mode. $\Delta f_o$ is then set to 600 Hz. The piezoelectric material is thus driven at frequency between 5.6 kHz and 6.6 kHz.

As mentioned above, the piezoelectric material generates heat when it is actuated. P. Belgrader et. al., (*Anal. Chem.*, 1999, 71:4232-4236) uses an insulant (coupler) between a PZT disc and the cell solution in order to prevent the increase in temperature from degrading the cells. Further, the PZT disc is external to the device. The insulant was necessary to prevent the heat from being easily conducted to the solution chamber. In fact, high temperature affects the quality of biomolecules, such as RNA, DNA and/or proteins. It is especially harmful to the RNA quality.

In the cartridge and/or biochip device of the invention, a lower voltage than that used by Belgrader et al. is applied so that an insulant (coupler) is not necessary and further, so that the PZT material can be inserted or integrated into the cartridge and/or biochip device of the invention. In fact, in the cartridge and/or biochip device of the invention, the PZT material is preferably actuated by applying a variable (modulated) frequency. Using a variable frequency to drive the PZT material, low heat is produced due to shorter disruption time and also an improvement in the cavitation efficiency. Accordingly, in a preferred aspect of the invention, the method of the invention comprises actuating the PZT by applying a variable frequency.

Figure 6:
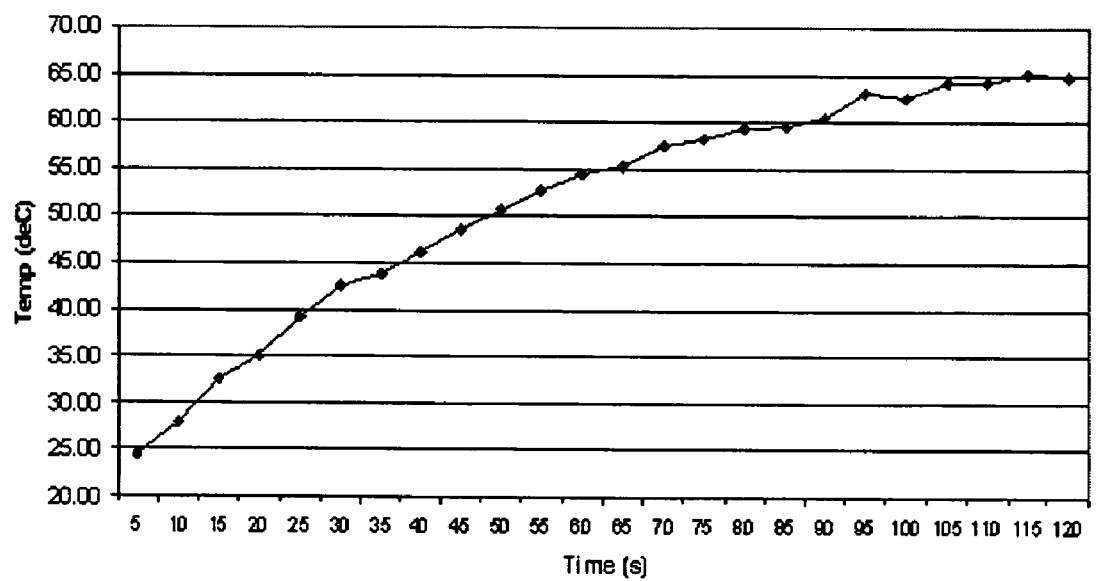
FIG. 6 shows the disruption chamber temperature changes with time.

FIG. 6 shows the disruption temperature rise in the cartridge and/or biochip device of the invention, measured by inserting a k type thermocouple and read out by a digital reader. Without any additional cooling, the chamber temperature rose from room temperature of 25° C. to a maximum of 66° C. As the disruption of the tissue and/or lysis of cells can be carried out in 5-40 seconds in the cartridge and/or biochip device of the invention, the rise of temperature is maintained between 25-45° C.

After the step of disruption of tissues and/or cell lysis, further steps may be carried out in the cartridge of the invention for the purification, isolation and detection of the analyte of interest. The analyte may be nucleic acids, proteins bacteria, virus, antigens, and the like. Methods known in the art may be applied for the purification, isolation and detection of the analyte. For example, in case of purification and isolation of nucleic acids, immunomagnetic capture beads, or beads coated with at least one linker comprising polyT-oligos or a linker complementary for a particular sequence of a specific nucleic acid may be used. The nucleic acid can then be recovered by using a magnet to trap the beads, washing out, and finally recovering the nucleic acids bound to the beads. For binding of the nucleic acids to the beads-linker or to the immunomagnetic capture beads, the PZT material can be actuated and used for improving the mixing and binding as described in the art. Further, the nucleic acid amplification (like RT-PCR, PCR, etc.) can be carried out directly in the chamber of the cartridge by adding the required reagents.

The cartridge is preferably a disposable (mono-use) device, which can be used independently for the treatment of biological samples, like biological tissues.

However, the cartridge of the invention can also be adapted to be inserted into an existing biochip device known in the art. It will be evident to any skilled person how to adapt or modify the cartridge shown in FIGS. 1 and 2, for example by adapting the inlet and outlet ports, to make the cartridge more suitable for insertion into a biochip. For example, the cartridge of the invention can be adapted to be inserted into the device of FIG. 9, more in particular inside the dissociation chamber.

The cartridge, for example, can be inserted or integrated into a biochip like a micro total analytical system (μ-TAS) or a lab-on-a-chip system. The advantage is that after use, the cartridge can be discarded and a new disposable cartridge is inserted into the biochip. This makes the whole process less prone to contamination.

Accordingly, the invention also provides a method of disrupting tissue and/or lysing cells in a cartridge or biochip comprising the steps:
- loading reagents and a sample;
- actuating a piezoelectric material, where the piezoelectric material is in contact with a second material, and wherein the second material has an uneven surface on an opposite side to that in contact with the piezoelectric material, the uneven surface contacting the sample;
- obtaining disrupted tissue and/or lysed cells; and
- recovering the eluate.

The PZT material is actuated by an external voltage source. The external voltage source supplies sinusoidal wave voltage having a peak-to-peak voltage, which is for example, from 50V to 400V. Any suitable sinusoidal wave voltage may be applied, this can also be of several thousand volts. It will be evident to a skilled person in the art how to choose the suitable voltage. In particular, the sinusoidal wave voltage has a peak-to-peak voltage from −300 to +300V, more in particular from −180 to +180V, preferably from −140V to +140V. The sinusoidal wave voltage has a scanning frequency, which may be from 1.0 kHz to 20 kHz. In particular, the scanning frequency is from 3.0 kHz and 8.0 kHz. More in particular, from 5.6 kHz to 6.6 kHz. Even more in particular, the scanning frequency is 3.3 kHz.

As mentioned above, the PZT material is preferably actuated by a variable (modulated) frequency. Using a variable (modulated) frequency to drive the PZT material, the cavitation result is strong and the heat produced is low. Accordingly, in a preferred aspect of the invention, the method of the invention comprises actuating the PZT material by applying a variable (modulated) frequency.

The biological sample may be a tissue from animal, human, plant, bacterial, virus and/or cell sample. The sample may be fresh or frozen tissue sample. The sample may also be cultivated cell, whole blood cell, serum, urine, saliva or tissue from biopsies. The disruption and/or cell lysis occur in a dissociation chamber of the cartridge.

The method further comprises the steps of isolating, purifying and/or amplifying nucleic acids obtained from the disrupted tissue and lysed cells, and recovering the nucleic acids. The reagents may further comprise washing buffer(s), elute buffer and/or RT-PCR reagent(s).

The nucleic acids may be recovered from the disrupted and/or lysed cells by adding beads coated with at least one linker, and recovering nucleic acids linked to the beads. The beads may be magnetic beads. The nucleic acids may be recovered by means of an external electromagnet field or permanent magnetic field. The binding of the linker on the beads to the nucleic acids may be carried out by actuating the piezoelectric material to increase the mixing and binding efficiency. The recovered nucleic molecules are DNA, RNA and/or mRNA.

The amount of tissue sample loaded into the cartridge and/or biochip device of the invention is between 0.1 mg to 100 mg. Also, the dissociation chamber may be preloaded with buffer.

According to a further embodiment, the invention provides a biochip comprising:
- a dissociation chamber;
- reagent and buffer reservoir(s);
- one or more valves;
- one or more pumps; and
- channels;

and with the proviso that there are no electrical connections integrated within the biochip.

The dissociation chamber may also be referred to as the disruption chamber.

The biochip comprises one or more pumps, wherein the pump is a micropump.

According to another aspect, the device may further comprise an injection hole. The device may also be modified such that automatic pumping can be carried out.

An example of the biochip (also indicated as biochip device) according to the invention is shown in FIG. 9. However, the biochip device of FIG. 9 already comprises the PZT discs.

The biochip of the invention may be made of any material suitable for a disposable biochip device. For example, a polymeric material. The polymeric material may be polycarbonate. The biochip device is conveniently transparent so as to be able to observe and verify the various steps of the reactions.

The biochip device is composed of at least three layers and one or more membranes for the valves and pumps. However, it may also be composed of four or more layers. These layers can be assembled together. Conveniently, the layers can be joint together, by using any assembling means or can be fused together according to standard methodologies known in the art. However, the cover layer is maintained as a removable layer. The first layer comprises at least the dissociation chamber, reagent and buffer reservoir(s) and part of channels. The second layer comprises at least the piezoelectric material. Further, the second layer comprises part of the channels which are connected to the channels arising from the chamber and reservoir(s) in the first layer, and wherein the valves and pumps are formed at an interface between the second and third layers. Further, there are channels formed at the interface between the second and third layers, as well as between the first and second layers. The biochip may further comprise a cover to put over the first layer. The cover helps in preventing the liquids in the device from spilling out when the PZT material is in motion.

In particular, the interface between the second and third layers comprises recesses for the valves and pumps. However, a person skilled in the art would be able to make modifications, in particular with respect to the position of the recesses within the device, which would enable the device to perform the same function.

The third layer may further comprise means of actuating the valves and pumps. In particular, the third layer may comprise vias which connect to a pneumatic source to actuate the valves.

An example of the structure of the biochip device can be seen in FIGS. 11A and 11B. FIG. 11A show the longitudinal (cross)-sectional view for the reservoir, pump, valve, channel and chamber connection, while FIG. 11B shows a different longitudinal (cross)-sectional view for the dissociation chamber, pump, valve, channel and chamber connection.

The first layer comprises the dissociation chamber and the reagent reservoir. It further comprises of channels routed from the reservoir and chamber respectively, through the interface of the first and second layers. The channels are further routed through the second layer into the third layer, leading to the pump unit and valve unit found at the interface of the second and third layers.

The biochip may further comprise a binding and mixing chamber. The biochip may also comprise an extraction/elute/PCR chamber.

FIG. 11A shows that the biochip comprises a reservoir and a chamber in the first layer, while FIG. 11B shows a biochip comprising a reservoir and a chamber. The chamber referred to in FIGS. 11A and 11B is the extraction/elute/PCR chamber. In both these figures, the mixing and binding chamber is not shown. Further, it should be noted that FIGS. 11A and 11B refer to the same biochip. However, the difference in the components of the first layer is due to the different longitudinal (cross)-sectional views referred to in each figure. Further, FIGS. 12A and 12B shows an enlarged view of the dissociation chamber within the biochip of FIG. 11.

Figure 10:
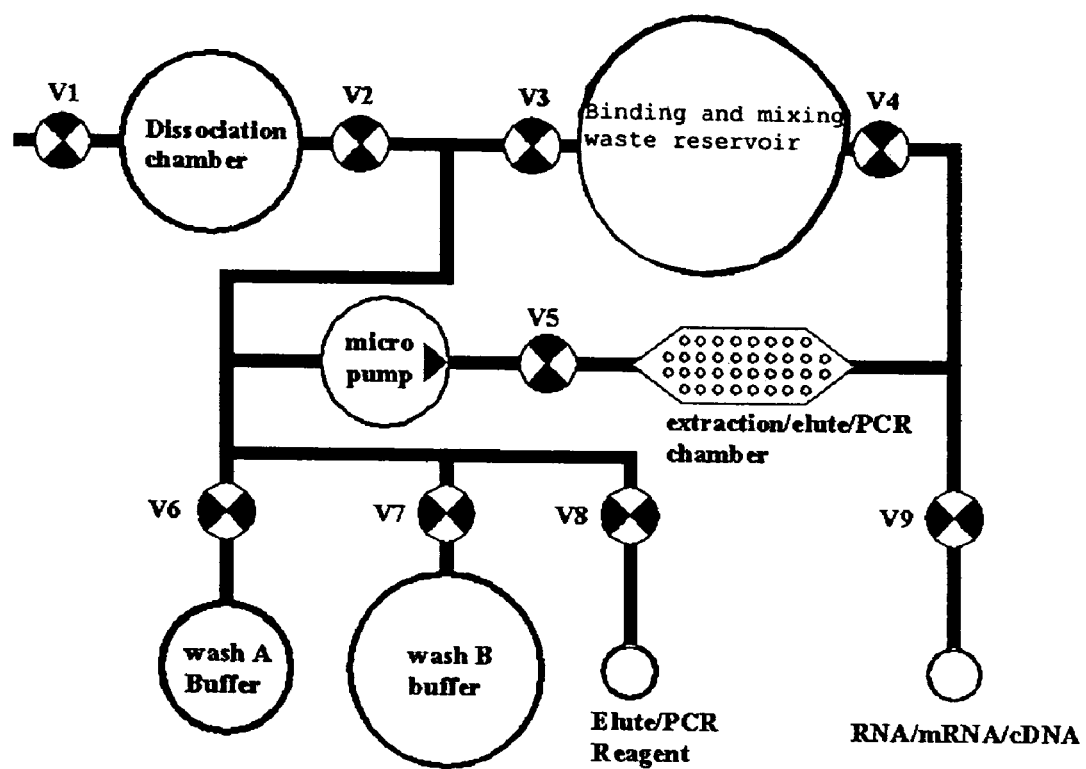
FIG. 10 shows a schematic structure of the biochip device.

The biochip device may also comprise a second chamber, which is the mixing and binding chamber (also indicated as "reservoir"), as shown in FIG. 9 and FIG. 10. Accordingly, the biochip device of the invention may also comprise a second PZT material (always in contact with a second material) in the binding and mixing chamber.

The at least three layers, the valve and micropump membranes and the cover layer may be made or purchased separately, and they are within the scope of the present invention. According to another aspect, the invention provides a kit comprising the at least three layers, the cover and optionally the membranes for the valves and pumps, and further one or more PZT material. The kit may also comprise the cover. The layers, membranes, and PZT material(s) can be jointed or assembled together before use. The joint or assembling can be carried out by using releasable fastening means known in the art. In alternative, the layers can be glued together or fused together according to know methodologies or technologies.

As mentioned above, the second material may be any suitable material to provide support for the PZT material to prevent it from bending during actuation. Accordingly, the second material has a Young's modulus of between 50 to 220 GPa. The second material may be a metal, a polymer, glass, and the like. The metal may be selected from the group consisting of steel, stainless steel, brass, copper and aluminium. However, other metals may also be used. The polymer material may be selected from a group consisting of polycarbonate, poly(methyl methacrylate) (PMMA), polyethylene, polypropylene, polystyrene and poly vinyl chloride (PVC). However, other known polymers may also be used.

The second material may have an uneven surface, which is in contact with the sample and/or cells. In particular, the uneven surface is brought about by a layer of silica beads. The silica beads may have a diameter between 100 and 400 µm. However, the surface of the second material in contact with the biological sample in the dissociating chamber may also have an even surface.

The PZT material may be in any suitable form, for example, a disc, rod or bar or a structure having a planar shape with at least 3 sides.

The PZT material needs to be actuated by an external voltage source. Accordingly, the PZT material and the second material comprises means, for example two electrodes, for actuating the PZT material. When the second material is a metal, one electrode will be connected to the PZT material and the second electrode, to the second material. However, when the second material is a non-conductive material, like a polymer material, then both the two electrodes will be connected to the PZT material. The means for connections or electrodes applied to the PZT material will preferably not be integrated into the cartridge. For example, two removable pins or other means for connection can be inserted into the biochip device to connect the external voltage source and the PZT material. The means for connection may be removable.

The valves of the biochip are microvalves. Membranes made of any suitable material known in the art are placed in the valve openings. The membranes of the microvalves are preferably made of poly(dimethylsiloxane) (PDMS). The microvalves are actuated by an external pneumatic source. The external pneumatic source supplies vacuum and/or compressed air to actuate the microvalves.

The biochip of the invention further comprises a membrane for a micropump. The micropump membrane may be made of poly(dimethylsiloxane) (PDMS). The micropump is actuated by an external pneumatic source. The external pneumatic source supplies vacuum and/or compressed air to actuate the micropump.

As shown in FIGS. 9 and 10, the biochip may further comprise an extraction/elute/PCR chamber. The extraction/elute/PCR chamber may be deposited with permalloy pins. An external electromagnet may be attached below the chamber in order to attract the magnetic beads linked or bound to the analyte (for example, to nucleic acids).

The binding and mixing chamber may comprise a further PZT material in contact with a second material in order to enhance the mixing and binding. Further, the binding and mixing chamber may comprise beads coated with at least one linker for binding to nucleic acid molecules, or immunomagnetic capture beads. Beads coated with at least one linker for binding to nucleic acid molecules may be magnetic beads.

The biochip may further comprise other components like biosensors, RT-PCR and microarrays, which can be integrated into the biochip. FIG. 10 shows the working process of the device. The micropump is the bulky microfluidic device. According to the design of the biochip of the invention, the number of micropumps used is reduced and they are replaced with microvalves to guide reagents. The biochip device shown in FIG. 10 consists of nine valves and a micropump for fluid manipulation; a PZT actuated chamber for tissue dissociation and a PZT actuated reservoir for bead-mRNA binding; and four reservoirs for storage of Washing buffer A, Washing buffer B, Elute/RT-PCR reagent and product (RNA, mRNA or cDNA, depending on requirements). mRNA extraction and PCR are performed inside a micro-chamber deposited with magnetic material, for example with permalloy, more in particular, with permalloy pins. An electromagnet may be positioned below the chamber.

FIG. 9 is a photograph of the prototype device. The pump and valves for manipulating fluidics are actuated by an external pneumatic source.

As seen in FIG. 10, reagents are preloaded into their respective reservoirs and chambers before the device is used. A tissue sample, weighing from 0.1 mg to 100 mg, is placed into dissociation chamber preloaded with 70 µl to 100 µl of PBS buffer. A PZT material coated with silica beads is actuated to generate strong cavitation and impact force to the tissue sample and this disintegrates the sample within 60 seconds. Cells of the tissue sample are completely lysed at the same time. Valves V1-V2, V4-V5 are opened and the micropump is switched on. The dissociated biological solution containing biomolecules is passed into the binding and mixing reservoir that has been preloaded with binding buffer and magnetic beads. This reservoir also has a built-in PZT material for enhancing the mixing efficiency. When the magnetic beads (coated with Oligo dT) are mixed with the lysate tissue solution, the mRNA is captured by Oligo dT and binds to the magnetic beads' surface. Valves V3, V4, V5 are opened and micropumping is carried out instantaneously to move the magnetic beads to the extraction and PCR chamber for elution. The electromagnet is functional at this time. The micropump is left on for a longer time so that the reagents inside the binding chamber can pass through the extraction/PCR chamber a few times to ensure that almost all the beads are recovered into the extraction/PCR chamber. When valve V3 closes, the binding reservoir is used for the storage of waste materials and chemicals. After the beads have been trapped in the extraction/PCR chamber, V6 is first opened followed by V7 so that Washing buffer A and Washing buffer B can pass to the chamber for mRNA purification. In the last step, valve V8 is opened and elution buffer or PCR reagent is pumped to the extraction/PCR chamber for mRNA elution or PCR amplification. The processing time from tissue loading to mRNA elution will take about 15 minutes (PCR thermal cycling is not included). Most of the time is spent in the mRNA purifying processes.

Integrated Polymeric Micropump for Reagent Delivery

The micropump used in the biochip device must generate sufficient pressure to propel fluid from one location through microchannels to another specific location. The most promising approach is the concept of a diaphragm pump, in which the chamber is bounded either by two check valves or two nozzle/diffuser configurations. A number of micro-pumps based on different actuating principles and fabricated by different technologies have been reported and developed in recent years [Disier Maillefer, et al., MEMS 1999, Orlando, Fla.; R. Linnemann, et al., The 11$^{th}$ annual international workshop on MEMS, 1998, Heidelberg German, pp. 532-5371].

For a membrane pump, it is essential to achieve a maximum compression ratio for high-performance processes like self-priming and bubble tolerance. The compression ratio is defined as:

$$\epsilon = (\Delta V + V_0)/V_0$$

Here, $\Delta V$ is the stroke volume and $V_0$ is the dead volume. The dead volume must be minimized and the stroke volume must be maximized in order to achieve a higher compression ratio.

Piezoelectric actuators, shape memory alloys, electrostatic actuators and thereto-pneumatic actuators have been used as actuating micropumps. These pumps require complicated fabrication processes, but generate only limited flow rate and relatively low pressure since the micro actuators are capable of generating limited force. The stroke volume of the pump is also limited. Hence good pump performance is hard to achieve. Furthermore, they are too costly for disposable applications like the biochip device of the present invention.

In the design of the biochip of the invention, a PDMS material, which has a low Young's modulus (20 Mpa), high elongation, biocompatibility and good sealing property was selected as the actuator membrane and the inlet/outlet valve membrane. Relatively high compression ratio enables the micropump to achieve self-priming and bubble tolerance. There is no back flow due to the good sealing property of PDMS. Polycarbonate plates have multiple functions, firstly, for the construction of the biochip device, and secondly for the formation of the pump housings and valve housings.

The PDMS membrane, the upper and lower pump housings form an airtight pump chamber. Compressed air and vacuum are applied to actuate the micropump. The depth of the micropump chamber in the upper pump housing and lower pump housing may be 200 µm. This limits the deflection of the PDMS actuation membrane; hence the precise stroke volume can be achieved. The flow rate is not sensitive to the pumping media viscosity, outlet and inlet pressure.

The external pneumatic source is connected to the bottom of the biochip device to actuate the pump. The inlet and outlet holes are formed in the connection layer and they communicate with the microchannels that are located in the reservoir layer.

PDMS is not photo definable and cannot be photo-lithographically patterned. In addition, it cannot be spun coated to achieve uniform thickness. Therefore, the PDMS membranes in our device are moulded by a micro mould. A two-part PDMS solution (Sylgardl84 Silicon Elastomer, Dow Corning) is used to cast the membrane. Part A and B of the solution are mixed in a 10:1 ratio. It is then poured slowly into the mould, followed by placing it in a vacuum dessicator for about one hour to release air bubbles trapped within the PDMS mixture. Once there are no visible air bubbles, a flat and smooth blade is used to traverse the upper surface of the mould while maintaining contact with the surface. This is to ensure the cured PDMS membrane has the same thickness as the depth of the mould. The whole set-up is then cured inside an oven at 70° C. for an hour. Finally, a PDMS membrane of uniform thickness is obtained and can be taken out of the mould.

A standalone pump is fabricated and characterized before integration into the biochip device. FIG. 13(A, B) shows the experimental results. When using water as the pumping media, the maximum pump head of 2 m was achieved. The flow rate was linear to the actuation frequency and independent of the output pressure (pump head).

Microvalve for Fluid Guidance

Another critical component in the biochip device is the microvalve. Micro check valves and micro active valves made from silicon material and polymer material have been reported. Although the check valve is simple in design, its inherent limitation such as a one-direction flow limits its usage. Moreover, in-built micro actuator active microvalves are too expansive to be used for disposable biochip application.

In the biochip of the invention, similar to our micropump structure, a simple PDMS membrane microvalve for fluid guidance has been designed. The microvalve is actuated by an external pneumatic source similar to that used in the micropump of the present invention.

The valve is constructed in the connection layer of the biochip device for easy communication to microchannels located in the reservoir layer. The flexibility of the PDMS membrane makes the valve functional at −0.1 atm pressure. It exhibits very good sealing property when it is closed. FIG. 14 shows its flow rate against the inlet pressure.

Multifunction Chamber for mRNA Extraction/PCR/elute

Magnetic bioseparation technology has been considered to be a very promising technique among several available biosample separation techniques. Its advantage is its ease of manipulation of biomolecules like DNA, RNA and mRNA. In the biochip device, Dynal Beads coated with Oligo(dT) on its surface are used for mRNA extraction. The beads are around 2.5 µm in diameter.

mRNA extracting, washing and PCR processing are done in the multifunction chamber of a volume of 20 µl. A metal plate coated with 10 µm polyimide (from P12525 from MicroChem) is placed at the bottom of the chamber. A miniature electric magnet is placed below the chamber to generate a magnetic field. When a DC current drives the electric magnet, the magnetic field will attract the beads and ensure that they remain in the chamber. When the electric magnet is driven by an alternative current, with frequency of 22 kHz, edged current is induced in the metal plate and they generate heat for PCR amplification. Heating rate of 16° C./s and cooling rate of 9.6° C./s are achieved. This non-contact heating method separates the heating component (the electric magnet) and sensor from the biochip device, hence making the biochip device more cost effective.

The invention further provides a method of disrupting tissue and/or lysing cells in a cartridge or biochip comprising the steps:

loading reagents and a sample;

actuating a piezoelectric material, where the piezoelectric material is in contact with a second material;

obtaining disrupted tissue and/or lysed cells; and recovering eluate.

The method of actuating the PZT material, disrupting the tissue and/or lysis the cells by actuation by means of an external voltage source is the same as that described above in the method of using the cartridge.

The biochip device comprises means for actuating the PZT material, for example, two electrodes as indicated above. When two PZT materials are present, that is, one in the dissociation chamber and one in the mixing and binding chamber, each PZT material has two electrodes.

The actuation of the piezoelectric material generates strong impact and cavitation to bring about the tissue disruption. The disruption and/or cell lysis occur in a dissociation chamber.

The sample loaded is usually between 0.1 mg to 100 mg. The sample may be tissue from animal, human, plant, or bacterial and/or virus sample. The sample may be fresh or frozen tissue sample. The sample may be cultivated cell, whole blood cell, serum, urine, saliva or tissue from biopsies.

The dissociation chamber may be preloaded with buffer.

The method further comprises the steps of isolating, purifying and/or amplifying nucleic acids obtained from the disrupted tissue and lysed cells, and recovering the nucleic acids. The reagents comprise washing buffer(s) and elute/RT PCR reagent(s).

The nucleic acids may be recovered from the disrupted and/or lysed cells by adding beads coated with at least one linker, and recovering nucleic acids linked to the beads. The beads may be magnetic beads. Alternatively, immunomagnetic capture beads may be used. The binding of the linker on the beads to the nucleic acids or the binding to the immunomagnetic capture beads may be carried out by actuating a second piezoelectric material to increase the mixing and binding efficiency.

The isolation, purification and/or amplification step may be carried out in a chamber as shown in FIGS. 9 and 10. The nucleic acids are recovered by means of an external electromagnet. The recovered nucleic molecules are DNA, RNA and/or mRNA.

Having now generally described the invention, the same will be more readily understood through reference to the following examples, which are provided by way of illustration, and are not intended to be limiting of the present invention.

EXAMPLES

The following example 1 was carried out on the cartridge (ex. FIGS. 1, 2), however, it is applicable also to the biochip device (ex. FIG. 9) of the invention.

Example 1

Cartridge and/or Biochip Device—Experimental Set-Up

Both fresh and frozen rat liver tissue samples, weighing 1 mg to 50 mg, were used for the experiments. The only pretreatment process, before inserting the tissues into the chamber of the cartridge through the inlet port, was to wash the tissue with water. This was to remove debris such as blood. Frozen tissue samples were derived from the freshly cut tissue in liquid nitrogen (−180° C.). The chamber proved to be capable of disrupting other tissues such as heart, muscle and kidney tissues.

The pre-processed tissue, together with 100 μl Phosphate Buffered Saline (PBS) was placed into the miniature cartridge chamber. The inlet port was sealed with a setscrew before driving the piezoelectric disc with the power amplifier. As the cartridge was transparent, the disruption process could be easily observed.

Fresh samples were cut directly from rat liver tissue, weighing between 5 mg and 50 mg. Rat liver tissue, heart tissue, muscle tissue and kidney tissue were used for the experiment successfully.

The effect of the cartridge chamber temperature on the nucleic acids, was investigated by inserting a miniature K type thermocouple into the chamber for measuring the temperature.

Disruption Time and Tissue Size

Figure 4:
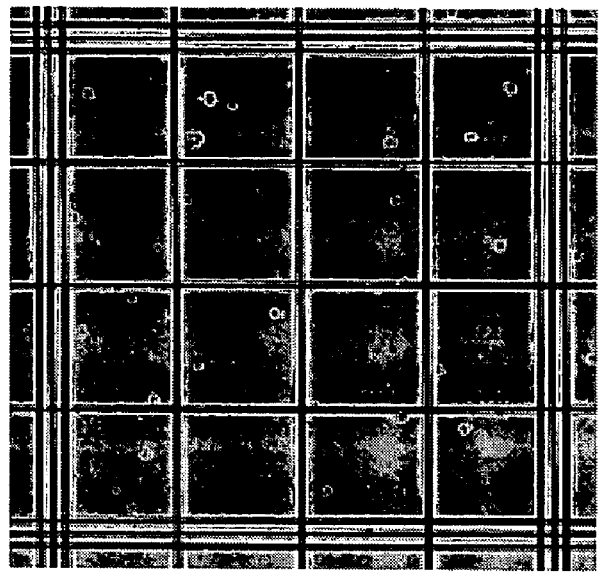
FIGS. 4(A) and 4(B) are optical images of the disrupted solution containing cell debris (a) from rat liver tissue, (b) from rat heart tissue. The grid distance is 100 μm.
Figure 4:
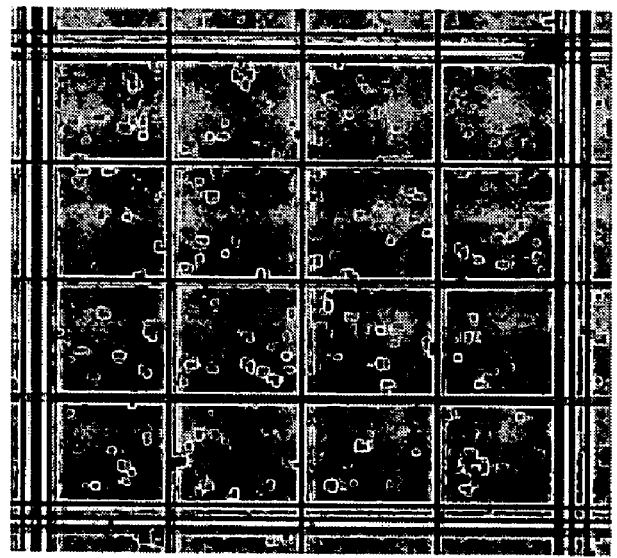

FIGS. 4(A) and (B) show the organized solution for a 10 mg rat fresh liver tissue disrupted with 100 μl PBS solution in 20 seconds. The tissue was fully disrupted to particles smaller than 7.8 μm in diameter. No cells were observed in the solution. This implied that cells contained inside the tissue had been lysed in the disruption step.

Figure 5:
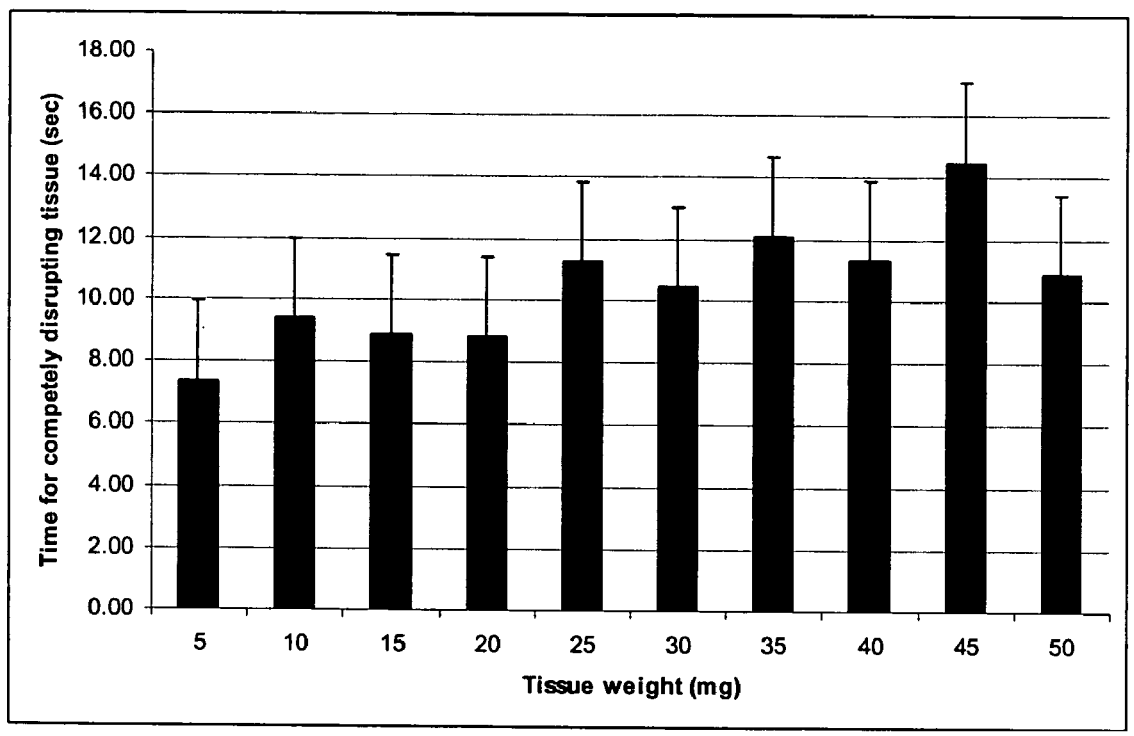
FIG. 5 shows the average disruption time (s) vs. the tissue sample weight (mg). The disruption efficiency is in terms of the initial tissue size disrupted by required time that is determined by optical images.

Time was recorded for comparing the disruption time and the size of tissue sample. The applied driving voltage and frequency was $250V_{pp}$, and 6.2 kHz respectively. Each sample weight was measured three times. FIG. 5 shows the experimental results. For tissue weight ranging from 25 mg to 50 mg, the time for full disruption was almost the same and they are less than 13 seconds. Smaller amounts of tissue and cell samples required less time for the process.

Frozen tissue samples gave similar results but the disruption time was slightly reduced. Frozen tissue is harder than fresh tissue and therefore they are easier to be disrupted by the chamber.

Actuation Time and Chamber Temperature

The piezoelectric disc will generate heat when it is actuated. High temperature will affect the quality of the biomolecules. It is especially harmful to the RNA quality. In order to verify whether or not the heat was easily conducted to the disruption chamber containing the undisrupted tissue and the organized tissue solution mixture in the chamber of the cartridge of the invention, the disruption temperature rise was measured by inserting a k type thermocouple and read out by a digital reader. The change in disruption chamber temperature is shown in FIG. 6. Without any additional cooling, the chamber temperature rise was maintained to a maximum of 66° C.

Gene Quality Testing

Total RNA and mRNA quality tests were performed using traditional extraction methods. Both rat liver fresh tissue and frozen tissue were used. The tests used homogenizer disruption and miniature chamber disruption independently.

Gene Quality Checking

The purification and yield OD testing was performed by Agilent BioChem Workstation 84X equipment. For fresh tissue and frozen tissue, the average ratio of A280/A260 was 1.98 and 1.99 respectively, very close to fresh tissue disrupted by homogenizer with a ratio of 2.00.

Figure 7:
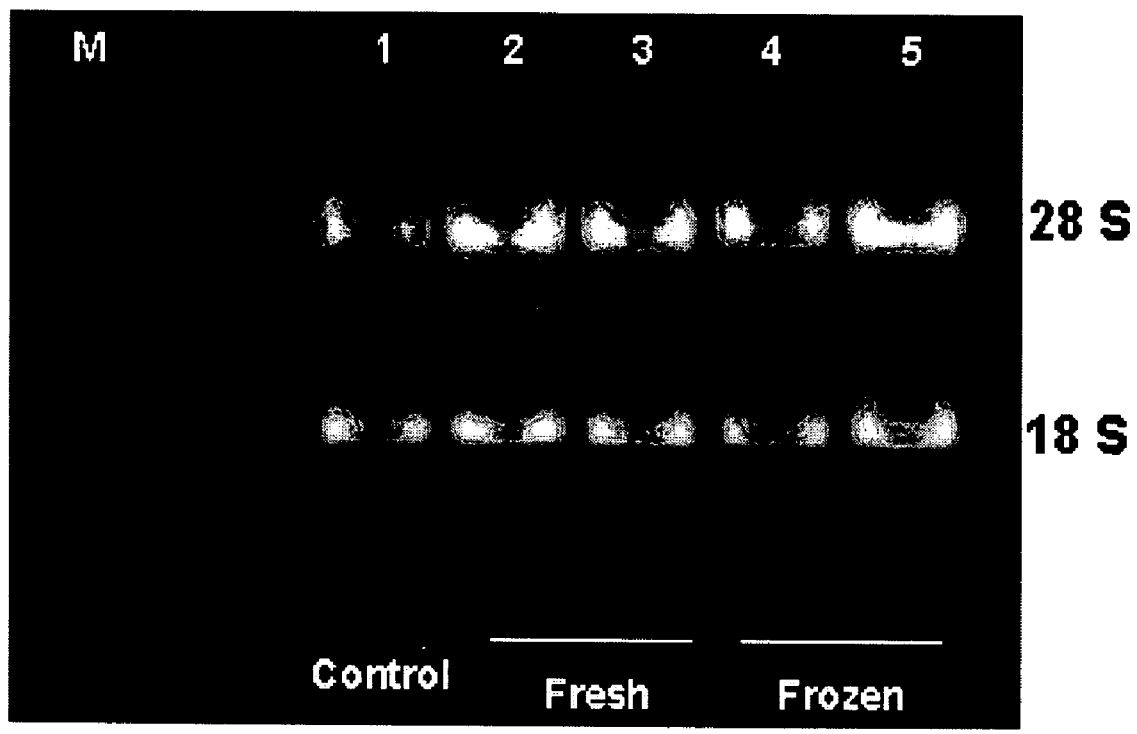
FIG. 7 shows agarose gel electrophoresis result of the RNA. From left to right: M: marker, 1: fresh tissue disrupted by homogenizer; 2 and 3: fresh tissue disrupted by the miniature chamber; 4 and 5: frozen tissue disrupted by the miniature chamber. 18S and 28S show the position of the 18S and 28S ribosomal RNAs respectively.

As shown in FIG. 7, the total RNA yield test was also performed using the above-mentioned equipment. The average total RNA yield for fresh tissue and frozen tissue by the disruption chamber was 5.50 µg and 5.45 µg respectively, comparable with fresh tissue disrupted by homogenizer which had a yield of 5.40 µg.

The mRNA was extracted by Dynal Oligo (dT) magnetic beads and purified by the washing buffer. Selected breast tumour related genes and housekeeping genes such as CD59, keratin19, TP53, Beta-actin, GAPDH, Cyclophilin and β-microglobulin were amplified by RT-PCR for 30 cycles using MJ Research PTC-200. The RT-PCT primers were from Sigmat HSRT-100 DuraScript RT-PCR Kit.

Figure 8:
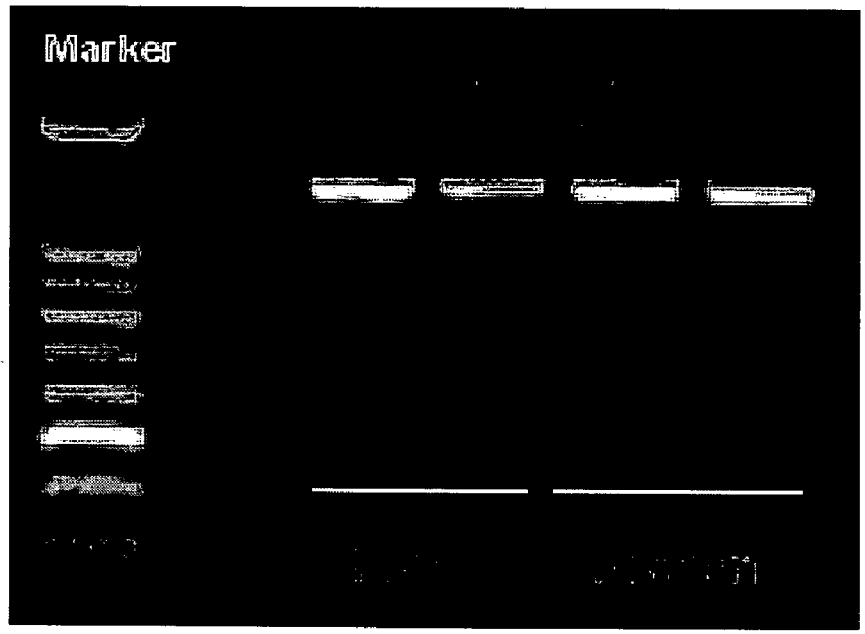
FIG. 8(A) shows agarose gel results for the RT-PCR product of the TP53 gene extracted from fresh tissue and frozen tissue. The longest mRNA in our test is 1176 bps.
FIG. 8(B) shows the same result for the shortest cDNA with 360 bps, β-microglobulin.
Figure 8:
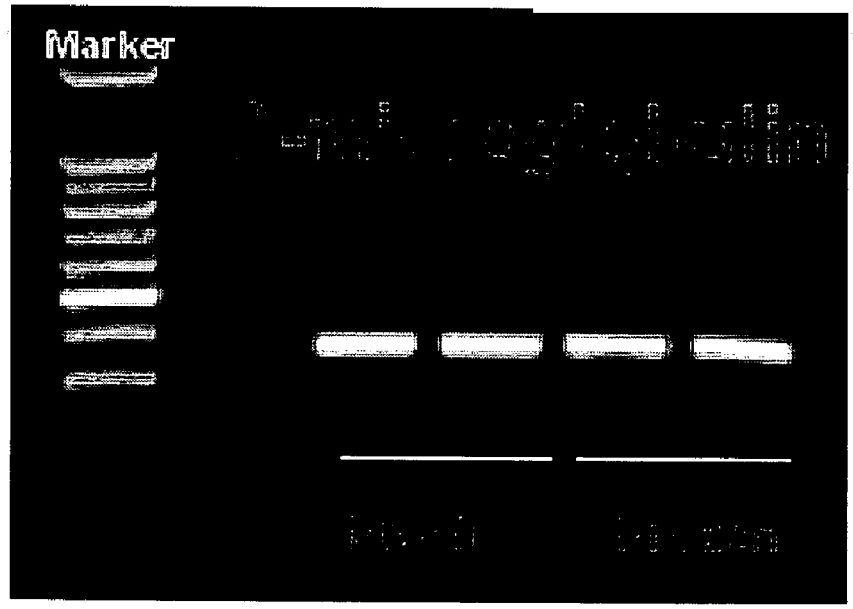

FIG. 8(A) shows agarose gel results for the TP53 mRNA extracted from fresh tissue and frozen tissue. The cDNA is then obtained from RT-PCR. The longest full-length cDNA in our test is 1176 bps. FIG. 8(B) shows the same result for the shortest of 360 bps, β-microglobulin. From the figures, the extracted mRNA is intact and it is in the correct position in the gel picture. The yield of the mRNA was 0.155 µg/mg tissue.

CONCLUSION

The prototype miniature cartridge of the invention for rapid and simultaneous mammalian tissue disruption and cell lysis was used. The tissue disruption was carried out within 30 seconds by scanning frequency high voltage driving method. The total RNA and mRNA yield were about 5.45 µg and 0.155 µg/mg, respectively, for every mg fresh or frozen tissue. Gel electrophoresis showed that intact RNA and mRNA were obtained. Accordingly, the disposable cartridge of the invention, as shown in FIGS. 1 and 2, has proven to be an easy-to-use, efficient, and quick device for the disruption of tissue and recovery of nucleic acid molecules. Accordingly, the cartridge may be used as an efficient device for the detection of genes. In particular, wherein the biological sample is a tissue from biopsies, the cartridge of the invention represents an efficient diagnostic method for determination of cancer biomarkers and gene-related analysis.

Example 2

Biochip Device (FIG. 9 and FIG. 10)

In the biochip device of the invention (FIGS. 9, 10 and 11), a miniature cavitation chamber for mammal tissue disruption and cell lysis is used simultaneously. The chamber utilizes a PZT disc as an actuator to generate a strong impact and cavitation for fresh or frozen tissue dissociation. On one surface of a 0.2 mm thick 15 mm in diameter brass disc, a layer of glue (Araldite—Rapid) is applied to adhere silica beads to its surface. On the other surface, a 10 mm in diameter piezoelectric disk (PXE5 from PHILIPS™) is glued. The silica beads, which have very sharp edges, are glued onto the surface of the disk opposite the piezoelectric disk side. The beads that are used vary from 100 µm to 400 µm in diameter. They are commonly found in water jet machines, which employ high-pressure water from a nozzle to cut metals. This specially made PZT disc is used to achieve maximum dissociation efficiency.

The tissue dissociation chamber has dimensions of 14.5 mm by 0.7 mm, with a volume of 115 µl. Tissues and reagents were loaded into the chamber via an inlet at the sidewall of the chamber.

Although piezoelectric actuator offers advantages such as compact size and high energy density, piezoelectric disk requires a relative high voltage for actuation [Madou, Marc J., CRC press, 1997, 416-419]. A lab-made power amplifier, with an output sinusoidal wave of 280V peak-to-peak voltage and a scanning frequency of 3 Hz was used to actuate the PZT disc (however, a scanning frequency of 5.4 kHz to 6.6 kHz can be used). Experiments showed that with scanning frequency, stronger cavitation was obtained in the tissue dissociation chamber, hence improving the tissue dissociation performance.

The same experiment showing the time required for full dissociation of rat liver tissue for different tissue sizes as described in Example 1 was carried out. The results are shown in FIGS. 4(A) and (B) and FIG. 5.

The invention claimed is:

1. A device for sample tissue disruption and/or cell lysis comprising: a piezoelectric material; and at least a second material in contact with the piezoelectric material; wherein the second material has an uneven surface on an opposite side to that in contact with the piezoelectric material, wherein the uneven surface is brought about by a layer of silica beads and contacts a biological sample.

2. The device of claim 1, wherein the second material is glued or fastened to the piezoelectric material.

3. The device of claim 1, wherein the silica beads have a diameter between 100 and 400 µm.

4. The device of claim 1, wherein the second material has a Young's modulus of between 50 to 220 GPa.

5. The device of claim 1, wherein the piezoelectric material is in the form of a disc, rod or bar or has a planar shape with at least 3 sides.

6. The device of claim 1, wherein the device is disposable.

7. The device of claim 1, wherein the device is a cartridge.

8. The device of claim 7, wherein the cartridge further comprises an inlet port, and outlet port, and at least one chamber.

9. The device of claim 7, wherein the cartridge is integrated into a bio chip.

10. The device of claim 1, wherein the device is a biochip device and further comprises:
a dissociation chamber;
reagent and buffer reservoir(s);
one or more valves;
one or more pumps; and
channels connecting the chamber, reservoir(s) and valve(s).

11. The device of claim 10, wherein the device further comprises a binding and mixing chamber and/or an extraction/elute/PCR chamber.

12. The device of claim 11, wherein the binding and mixing chamber comprises a piezoelectric material and a second material in contact with the piezoelectric material.

13. The device of claim 11, wherein the extraction/elute/PCR chamber is deposited with magnetic material.

14. The device of claim 11, wherein the binding and mixing chamber comprises beads coated with at least one linker for binding to nucleic acid molecules.

15. The device of claim 14, wherein the beads are magnetic beads.

16. The device of claim 10, wherein the valves are microvalves.

17. The device of claim 16, wherein the microvalves comprise membrane microvalves made of material including poly(dimethylsiloxane) (PDMS).

18. The device of claim 10, wherein the pump is a micropump and comprises a membrane.

19. The device of claim 18, wherein the membrane is made of material including poly(dimethylsiloxane) (PDMS).

20. The device of claim 10, wherein the biochip is composed of at least three layers, one or more membranes for the valves and one or more membranes for the pumps, and wherein the first layer comprises at least the dissociation chamber, reagent and buffer reservoir(s), the second layer comprises at least the piezoelectric material, and wherein the valves and the pumps are found at an interface between the second and third layers, and the channels are found at the interfaces of the first and second, and the second and third layers.

21. The biochip of claim 20, further comprising a cover to put over the first layer.

22. A method of disrupting tissue and/or lysing cells in a device, comprising the steps of:
loading a sample and reagents in a device;
actuating a piezoelectric material of the device, wherein the piezoelectric material is in contact with a second material, wherein the second material has an uneven surface on an opposite side to that in contact with the piezoelectric material, the uneven surface contacting the sample, and wherein the uneven surface is brought about by a layer of silica beads;
obtaining disrupted tissue and/or lysed cells; and
recovering the eluate.

23. The method of claim 22, wherein the silica beads have a diameter between 100 and 400 μm.

24. The method of claim 22, wherein the piezoelectric material is actuated by an external voltage source.

25. The method of claim 24, wherein the external voltage source supplies a variable frequency voltage to actuate the piezoelectric material.

26. The method of claim 22, wherein the sample is an animal, human, plant, or adipose-originated tissue and/or cell sample.

27. The method of claim 26, wherein the sample is fresh or frozen tissue and/or cell sample.

28. The method of claim 22, further comprising the steps of isolating, purifying and/or amplifying nucleic acids obtained from the disrupted tissue and lysed cells, and recovering the nucleic acids.

29. The method of claim 28, wherein the nucleic acids are recovered from the disrupted and/or lysed cells by adding beads coated with at least one linker, and wherein the binding of the linker on the beads to the nucleic acids is carried out by actuating a second piezoelectric material to increase the mixing and binding efficiency, and recovering nucleic acids linked to the beads.

30. A piezoelectric device comprising a piezoelectric material, which is in contact with at least a second material; wherein the second material has an uneven surface on an opposite side to that in contact with the piezoelectric material, wherein the uneven surface is brought about by a layer of silica beads, and wherein the uneven surface contacts a biological sample.

31. The piezoelectric device of claim 30, wherein the silica beads have a diameter between 100 and 400 μm.

32. The piezoelectric device of claim 30, wherein the second material has a Young's modulus of between 50 to 220 GPa.

33. The piezoelectric device of claim 30, wherein the piezoelectric material is in the form of a disc, rod or bar or has a planar shape with at least 3 sides.

* * * * *

UNITED STATES PATENT AND TRADEMARK OFFICE
CERTIFICATE OF CORRECTION

PATENT NO. : 7,611,840 B2  Page 1 of 1
APPLICATION NO. : 10/910961
DATED : November 3, 2009
INVENTOR(S) : Guolin Xu et al.

It is certified that error appears in the above-identified patent and that said Letters Patent is hereby corrected as shown below:

Title Page, Item 56

"Anonymous, "Ultrasonic probe for rapid processing of small liq. samples minimising tip erosion and heating – has specified concavity at tip to focus sound filed and overcome edge sound dispersion effects," Derwent Abstract Accession No. 93-342956/43, Research Disclosure 353012A, Sep 10, 1993" should read --Anonymous, "Ultrasonic probe for rapid processing of small liq. samples minimising tip erosion and heating – has specified concavity at tip to focus sound field and overcome edge sound dispersion effects," Derwent Abstract Accession No. 93-342956/43, Class S03, Research Disclosure 353012A, Sep. 10, 1993--.

Column 18
Line 41, "comprises an inlet port, and outlet port, and at least one" should read --comprises an inlet port, an outlet port, and at least one--.

Signed and Sealed this

Twenty-third Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,611,840 B2
APPLICATION NO. : 10/910961
DATED : November 3, 2009
INVENTOR(S) : Xu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1433 days.

Signed and Sealed this

Twelfth Day of October, 2010

David J. Kappos
*Director of the United States Patent and Trademark Office*